United States Patent
Houjou et al.

(10) Patent No.: US 9,060,684 B2
(45) Date of Patent: Jun. 23, 2015

(54) OBSERVATION DEVICE, OBSERVATION PROGRAM, AND OBSERVATION SYSTEM

(75) Inventors: Mikio Houjou, Osaka (JP); Atsushi Oda, Osaka (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 159 days.

(21) Appl. No.: 13/808,520

(22) PCT Filed: Aug. 30, 2011

(86) PCT No.: PCT/JP2011/069672
§ 371 (c)(1),
(2), (4) Date: Feb. 25, 2013

(87) PCT Pub. No.: WO2012/029817
PCT Pub. Date: Mar. 8, 2012

(65) Prior Publication Data
US 2013/0156287 A1 Jun. 20, 2013

(30) Foreign Application Priority Data
Aug. 30, 2010 (JP) .................................. 2010-192485

(51) Int. Cl.
G06K 9/00 (2006.01)
A61B 5/00 (2006.01)
G01N 21/13 (2006.01)
G02B 21/00 (2006.01)
G02B 21/36 (2006.01)
C12M 1/34 (2006.01)

(52) U.S. Cl.
CPC .............. *A61B 5/0033* (2013.01); *G01N 21/13* (2013.01); *G02B 21/0088* (2013.01); *G02B 21/365* (2013.01); *C12M 41/36* (2013.01)

(58) Field of Classification Search
CPC .. A61B 5/0033; G01N 21/13; G02B 21/0088; G02B 21/365; C12M 41/36
See application file for complete search history.

(56) References Cited

U.S. PATENT DOCUMENTS 6,330,349 B1 * 12/2001 Hays et al. ..................... 382/128
7,689,038 B2 * 3/2010 Zahniser ....................... 382/180
(Continued)

FOREIGN PATENT DOCUMENTS

| JP | 2002-148526 A | | 5/2002 | |
|----|---------------|---|--------|---|
| JP | 2008-076530 A | | 4/2008 | |
| JP | 2008-233608 A | | 10/2008 | |
| JP | WO 2009110462 | * | 3/2009 | ............... C12Q 1/02 |

(Continued)

*Primary Examiner* — Katrina Fujita
(74) *Attorney, Agent, or Firm* — McDermott Will & Emery LLP

(57) ABSTRACT

An observation device (1) is provided with: a general observation unit (10) for observing sample cells by observing an entire container (C) containing the cells and a culture solution; and a magnification observation unit (20) for magnifying a region within the container (C) and observing the cells, the general observation unit (10) and the magnification observation unit (20) each individually having lighting for illuminating the cells with light, and an optical system for observing the cells. The general observation unit (10) and the magnification observation unit (20) are thereby each provided with an individual optical system and lighting, making it possible to configure an appropriate observation unit for use both when the cells are observed by observing the entire container (C) and when a part within the container (C) is magnified and the cells are observed.

7 Claims, 14 Drawing Sheets

(56) References Cited

U.S. PATENT DOCUMENTS

| | | | |
|---|---|---|---|
| 8,478,017 B2* | 7/2013 | Mimura et al. | 382/133 |
| 2002/0060842 A1 | 5/2002 | Ogino et al. | |
| 2007/0139638 A1 | 6/2007 | Wolpert et al. | |
| 2010/0128961 A1 | 5/2010 | Kalusche | |
| 2010/0208960 A1* | 8/2010 | Kiyota | 382/128 |

FOREIGN PATENT DOCUMENTS

| | | |
|---|---|---|
| JP | 2009-520991 A | 5/2009 |
| JP | 2009-198709 A | 9/2009 |
| JP | 2009-282198 A | 12/2009 |
| WO | WO-2008/137912 A1 | 11/2008 |

* cited by examiner

OBSERVATION DEVICE, OBSERVATION PROGRAM, AND OBSERVATION SYSTEM

RELATED APPLICATIONS

This application is the U.S. National Phase under 35 U.S.C. §371 of International Application No. PCT/JP2011/069672, filed on Aug. 30, 2011, which in turn claims the benefit of Japanese Application No. 2010-192485, filed on Aug. 30, 2010, the disclosures of which Applications are incorporated by reference herein.

TECHNICAL FIELD

The present invention relates to an observation device, an observation program, and an observation system for observation of a sample such as biological or other cells.

BACKGROUND ART

In the culturing of cells, an ability to start observation simultaneously with occurrence of a cell mass, which is a mass of a plurality of cells, and then continue the observation along the time axis can be said to be a promising technology that may assist, for example, regenerative medicine. Conventionally, such observation of cells is performed under a microscope during the culturing of the cells when the culture container needs to be replenished with the culture fluid or the culture fluid needs to be replaced, and images (photos) are taken as necessary.

However, cell observation using a microscope requires much trouble. For example, to identify cell masses that have occurred inside a container, it is necessary first to observe the entire container with the eye or through a microscope, and then, after switching to a magnified scale as by interchanging objective lenses, to proceed to observation of the growing condition of individual cell masses. Magnified observation suffers from a narrow view field, and this makes it difficult to find target cell masses and also to bring them into the view field. Moreover, in cell observation, time lapse observation is desired so that long-term change of cell masses can be observed every predetermined period from their occurrence till completion of their growth. Immediately after semination of cells, it is impossible to observe cell masses with the eye or through a low-magnification microscope, and this makes it necessary to search for them and set the observation positions anew after several days.

Moreover, with conventional observation, which is performed about once a day to three days when the culture container is replenished with the culture fluid or the culture fluid is replaced, it is difficult to observe cell masses from their occurrence, and thus there are strong demands for technologies that allow observation of cell masses from their occurrence. Furthermore, both in observation of an entire container and in observation of part of the inside of a container on a magnified scale, when images of cells are taken, inconveniently, the heat generated by an illuminator and a lens drive system affects the growth of the cells.

For such cell observation, there have been proposed devices that eliminate the trouble of switching between observation of an entire container and observation of part of the inside of a container on a magnified scale, and one example of such devices is seen in Patent Document 1 listed below. The observation device disclosed in Patent Document 1 is provided with at least two image sensing optical systems that take images of an observation target at different magnifications, and the reference value for the low-magnification image is calculated such that the feature quantity of the image taken through the high-magnification image sensing optical system is approximately equal to the feature quantity of the image taken simultaneously through the low-magnification image sensing optical system.

LIST OF CITATIONS

Patent Literature

Patent Document 1: Japanese Patent Application Publication No. 2009-198709

SUMMARY OF INVENTION

Technical Problem

However, in the observation device disclosed in Patent Document 1, the high-magnification and low-magnification image sensing optical systems use a common light source for their image sensing, and this makes it impossible to observe the details of cells inside a container. The reason is that, while the high-magnification image sensing optical system requires an illuminator, such as a point light source combined with a ring slit, as used in a phase contrast optical system that is suitable for observation of almost transparent cells in a very small region, the low-magnification image sensing optical system requires an illuminator, such as a planar light source, that is suitable for observation in a comparatively wide view field; thus, the two image sensing optical systems requires different illuminators. That is, there is fear that, while the distribution of cells inside a container can be observed, identification of cell masses that have occurred inside the container may fail, or target cell masses may be erroneously discriminated. Moreover, no consideration is given to continuous observation from occurrence of cell masses till completion of their growth.

Devised against the background discussed above, the present invention aims to provide an observation device that, in observation of a sample such as cells inside a container, allows observation of the entire container for identification of a sample mass having occurred and in addition allows magnification of the identified sample for observation of their details. The invention also aims to provide an observation program and an observation system that allow continuous observation of cell masses from their occurrence till completion of their growth.

The invention further aims to provide an observation device that is compact despite allowing overall observation and magnified observation.

Solution to Problem

To achieve the above objects, according to the invention, an observation device includes: an overall observation portion for observation of a sample through observation of an entire container containing the sample and a solution; and a magnified observation portion for observation of the sample through observation of a partial region within the container on a magnified scale. The overall observation portion and the magnified observation portion each individually include an illuminator which shines light on the sample and an optical system for observation of the sample.

With this configuration, the overall observation portion and the magnified observation portion have separate illuminators and optical systems respectively. Thus, it is possible to configure an observation portion adequate both for observation of the sample through observation of the entire container and for observation of the sample through magnification of part of the inside of the container. In this way, it is possible to observe the entire container and identify a sample mass that has occurred, and in addition to magnify the identified sample mass and observe its details.

In the observation device configured as described above, the overall observation portion and the magnified observation portion may each include an image sensing portion which takes an image of the sample inside the container.

With this configuration, the taken image is stored, and this makes it easy to identify a sample mass and observe its details.

In the observation device configured as described above, the overall observation portion may include an overall observation illuminator arranged below the container and an overall observation optical system arranged above the container, and the magnified observation portion may include a magnified observation illuminator arranged above the container and a magnified observation optical system arranged below the container.

With this configuration, in the overall observation portion, the sample is irradiated with light from below the container, and this makes it possible to irradiate it with light adequate to identify a sample mass that occurs and grows near the inner bottom face of the container. Moreover, the magnified observation optical system which is comparatively heavy by having a plurality of lenses and a zoom mechanism for them for magnified observation of the sample in the magnified observation portion is arranged in a lower part. This gives the device a proper weight balance and thereby allows stable magnified observation.

In the observation device configured as described above, there may be further provided a transport portion which transports the container from the overall observation portion to the magnified observation portion or in the reverse direction.

With this configuration, the container is transported, and thus even when the overall observation portion and the magnified observation portion are arranged at a distance from each other, it is possible to observe the entire container and identify a sample mass that has occurred, and in addition to magnify the identified sample mass and observe its details.

In the observation device configured as described above, the transport portion may transport the container in transport directions perpendicular to the optical axis direction of the overall observation portion and the magnified observation portion, and at least one of the transport directions may be common to the overall observation portion and the magnified observation portion such that coordinates within the observation view field in the overall observation portion coincide coordinates within the observation view field in the magnified observation portion.

With this configuration, coordinates within the observation view field coincide between the overall observation portion and the magnified observation portion, and this makes it easy to discriminate in the magnified observation portion the sample mass identified through observation of the entire container in the overall observation portion. This prevents erroneous discrimination of a target sample mass, and thus allows observation with high precision.

In the observation device configured as described above, the overall observation portion and the magnified observation portion may be provided inside an airtight casing; in the overall observation portion, the overall observation illuminator may be arranged with a gap from the container; and in the magnified observation portion, only a part around a lens portion included in the magnified observation optical system closest to the bottom face of the container may be covered by a cover member having a window.

With this configuration, in the overall observation portion, between the overall observation illuminator and the container, a space is left through which air can pass, and this makes it difficult for the heat generated by the illuminator to be conducted to the container. Moreover, in the magnified observation portion, between the magnified observation optical system and the container, a cover member having a window is provided which covers only a part around the lens portion closest to the bottom face of the container, and this makes it difficult for the heat generated by the magnified observation optical system to be conducted to the container. With these features, it is possible to suppress the effect of the heat generated by an illuminator and a lens drive system on the growth of the sample.

To achieve the above objects, according to the invention, an observation program makes a computer execute processing including: overall image sensing processing for taking an image of a sample through taking an image of an entire container containing the sample and a solution; sample mass discrimination processing for discriminating from the image taken in the overall image sensing processing a sample mass, which is a mass of a plurality of pieces of the sample; coordinate detection processing for detecting the coordinates of the center of the sample mass discriminated in the sample mass discrimination processing; and magnified image sensing processing for taking an image of the sample mass through magnification about, as the center, the coordinates detected in the coordinate detection processing.

With this configuration, from the image resulting from taking the entire container, a sample mass is discriminated; then its coordinates are detected; and then, through magnification about, as the center, the detected coordinates, it is possible to observe the details of the sample mass.

In the observation program configured as described above, in the sample mass discrimination processing, of sample masses discriminated, a sample mass having a size equal to or larger than a predetermined size may be recognized as a magnified observation target sample mass; and in the coordinate detection processing, the coordinates of the center of the magnified observation target sample mass may be detected on condition that the magnified observation target sample mass has been recognized in the sample mass discrimination processing, and arbitrary coordinates may be detected on condition that no magnified observation target sample mass has been recognized in the sample mass discrimination processing.

With this configuration, a sample mass having a size equal to or larger than the predetermined size is recognized as a magnified observation target sample mass, and this makes it possible to grasp the time of occurrence of the sample mass. It is thus possible to perform continuous observation from occurrence of the sample mass till completion of its growth.

The "predetermined size" mentioned above is a previously set size of the sample mass, and is such a size as to permit a decision to take it as a magnified observation target; it may be defined, for example, in terms of the number of pixels on an image. For example, as one specific example of the number of pixels as the predetermined size of the sample mass is, in a case where overall observation is performed with a 5 megapixel camera by taking an image of a 40 mm×40 mm view field, about 1000 pixels is adequate as the set predetermined size. In the embodiments presented later, the "predetermined size" is set at, in terms of the number of pixels, "1000 pixels,"

but this is not meant as limitation to that size. The same applies to "predetermined size" used in other means mentioned further on.

In the observation program configured as described above, the processing may further include time keeping processing for counting days and hours from the start of observation of the sample; and, in the sample mass discrimination processing, discrimination of the magnified observation target sample mass may be repeated every predetermined period counted in the time keeping processing with respect to sample mass discrimination until the magnified observation target sample mass is recognized, and the discrimination of the magnified observation target sample mass may be stopped on condition that a predetermined number of days have elapsed.

With this configuration, discrimination of the magnified observation target sample mass is repeated every predetermined period with respect to sample mass discrimination until the magnified observation target sample mass is recognized, that is, until the time of occurrence of the sample mass is grasped, and this makes it possible to automatically grasp the time of occurrence of the sample mass. When the predetermined number of days have elapsed from the start of observation of the sample, discrimination of the magnified observation target sample mass is stopped. Thus, magnified observation of only a sample mass identified in overall observation is performed, and it is possible to proceed with observation efficiently till completion of growth.

The "predetermined period with respect to sample mass discrimination" mentioned above is a previously set period with respect to the timing with which discrimination of the magnified observation target sample mass is performed, and is such a period as to permit grasping of the time of occurrence of the sample mass; it may be, for example, a period of several hours to several days, and may be set appropriately as necessary. Thus, although, in the embodiments presented later, the "predetermined period with respect to sample mass discrimination" is set at "one day," this is not meant to be limitation to that period. It should be noted that the term "predetermined period" used in other means does not always denote a period with respect to the timing with which discrimination of the magnified observation target sample mass is performed, nor does it denote a period that temporally coincides with it.

Likewise, the predetermined number of days" mentioned above is a previously set number of days with respect to the timing with which discrimination of the magnified observation target sample mass is ended, and may be set at an arbitrary number of days such as 5 days, 7 days, or 10 days. In the embodiments presented later, the "predetermined number of days" is set at "5 days," but this is not meant as limitation to that number of days.

In the observation program configured as described above, the processing may further include time keeping processing for counting days and hours from the start of observation of the sample; and, in the magnified image sensing processing, an image of the sample mass may be taken every predetermined period counted in the time keeping processing with respect to magnified image sensing, and image sensing may be stopped on condition that a predetermined deadline is reached.

With this configuration, a magnified image of the sample mass is taken every predetermined period with respect to magnified image sensing, and the image sensing is ended when the predetermined deadline is reached. This makes it possible to perform time lapse observation continuously from occurrence of the sample mass till completion of its growth.

The "predetermined period with respect to magnified image sensing" mentioned above is a previously set period with respect to the timing with which an image of the sample mass is taken on a magnified scale, and is such a period as to permit grasping of the growing process of the sample mass; it may be, for example, a period of several hours to several days, and may be set appropriately as necessary. Thus, although, in the embodiments presented later, the "predetermined period with respect to magnified image sensing" is set at "one day," this is not meant as limitation to that period. It should be noted that the term "predetermined period" used in other means does not always denote a period with respect to the timing with which a magnified image of the sample mass is taken, nor does it denote a period that temporally coincides with it.

Likewise, the "predetermined deadline" mentioned above is a previously set deadline with respect to the timing with which observation of the sample is ended, and may be set at an arbitrary deadline such as 10 days, 20 days, or 30 days from the start of observation of the sample. In the embodiments presented later, the "predetermined deadline" is set at "10 days," but this is not meant as limitation to that deadline.

In the observation program configured as described above, the processing may further include figure discrimination processing for discriminating from the image taken in the magnified image sensing processing a sample mass having a predetermined figure.

With this configuration, a sample mass having the predetermined figure is discriminated, and this makes it possible to automatically pick out a sample mass having a figure adequate for continued observation. In this way, it is possible to give lower priority to, or stop, observation of a sample mass that has grown to have a distorted figure, and thus to proceed with observation of a sample mass having an adequate figure more efficiently.

The "predetermined figure" mentioned above is a previously set figure of the sample mass, and is such a figure as to permit a judgment that it is likely to continue growing in a way adequate for observation; preferably, it is close to circular, and may be set as desired in terms of a value such as ellipticity. In the embodiments described later, the "predetermined figure" is set to have an "ellipticity of 1.1 or less," but this is not meant to limit to that figure.

To achieve the above objects, according to the present invention, an observation method includes: an overall image sensing step for taking an image of a sample through taking of a container containing the sample and a solution; a sample mass discrimination step for discriminating from the image taken in the overall image sensing step a sample mass, which is a mass of a plurality of pieces of the sample; a coordinate detection step for detecting the coordinates of the center of the sample mass discriminated in the sample mass discrimination step; and a magnified image sensing step for taking an image of the sample mass through magnification about, as the center, the coordinates detected in the coordinate detection processing.

With this configuration, from the image resulting from taking the entire container, a sample mass is discriminated; then its coordinates are detected; and then, through magnification about, as the center, the detected coordinates, it is possible to observe the details of the sample mass.

To achieve the above objects, according to the present invention, an observation system includes: an overall observation portion including an illuminator which shines light on a sample inside a container containing the sample and a solution and an optical system which guides light for observation of the sample, the overall observation portion taking an image of the sample through taking an image of the entire container; a time keeping portion which counts days and hours from the start of observation of the sample; a data processing portion which repeats discrimination of a sample mass, which is a mass of a plurality of pieces of the sample, every predetermined period counted by the time keeping portion with respect to sample mass discrimination until a sample mass having a size equal to or larger than a predetermined size is recognized from the image taken by the overall observation portion, the data processing portion detecting the coordinates of the center of the recognized sample mass having a size equal to or larger than the predetermined size, the data processing portion detecting arbitrary coordinates on condition that no sample mass having a size equal to or larger than the predetermined size has been recognized; a magnified observation portion including an illuminator which shines light on the sample inside the container and an optical system which guides light for observation of the sample, the magnified observation portion taking an image of the sample mass on a magnified scale about, as the center, the coordinates detected by the data processing portion; and a setting portion which sets the sample mass discrimination repetition deadline until which the data processing portion recognizes the sample mass having a size equal to or larger than the predetermined size, the timing with which the magnified observation portion takes the image, and the observation deadline until which the sample is observed.

With this configuration, from the image resulting from taking the entire container, a sample mass is discriminated; then its coordinates are detected; and then, through magnification about, as the center, the detected coordinates, it is possible to observe the details of the sample mass. Moreover, discrimination of the magnified observation target sample mass is repeated every predetermined period with respect to sample mass discrimination until the magnified observation target sample mass is recognized, that is, until the time of occurrence of the sample mass is grasped, and this makes it possible to automatically grasp the time of occurrence of the sample mass. When the predetermined number of days have elapsed from the start of observation of the sample, discrimination of the magnified observation target sample mass is stopped. Thus, magnified observation of only a sample mass identified in overall observation is performed, and it is possible to proceed with observation efficiently till completion of growth. Furthermore, a magnified image of the sample is taken with the predetermined timing, and when the observation deadline is reached, the image sensing is ended; thus, it is possible to perform time lapse observation continuously from occurrence of a sample mass till completion of its growth.

Advantageous Effects of the Invention

According to the present invention, it is possible to provide an observation device that, in observation of a sample such as cells being cultured inside a container, allows identification of a sample mass having occurred by observation of the entire container and in addition allows magnification of the identified sample mass for observation of their details. It is also possible to provide an observation program and an observation system that allow continuous observation of cell masses from their occurrence till completion of their growth.

Furthermore, for observation of a sample being cultured inside a container, a configuration is adopted where an optical axis of the optical system of an overall observation portion for observation of the entire container and an optical axis of the optical system of a magnified observation portion for observation of the sample through magnification of a partial region within the container coincide with each other, and this makes it possible to greatly reduce the size of the device compared with conventional ones.

DESCRIPTION OF EMBODIMENTS

Hereinafter, embodiments of the present invention will be described with reference to FIGS. 1 to 15. In the following description, cells are taken as a representative of samples (specimens) such as cells, bacteria, and microorganisms, and a solution is taken as a representative of culture fluids. Likewise, a cell mass, which is a mass of a plurality of cells flocked together, is taken as a representative of a sample mass.

(Embodiment 1)

Figure 1:
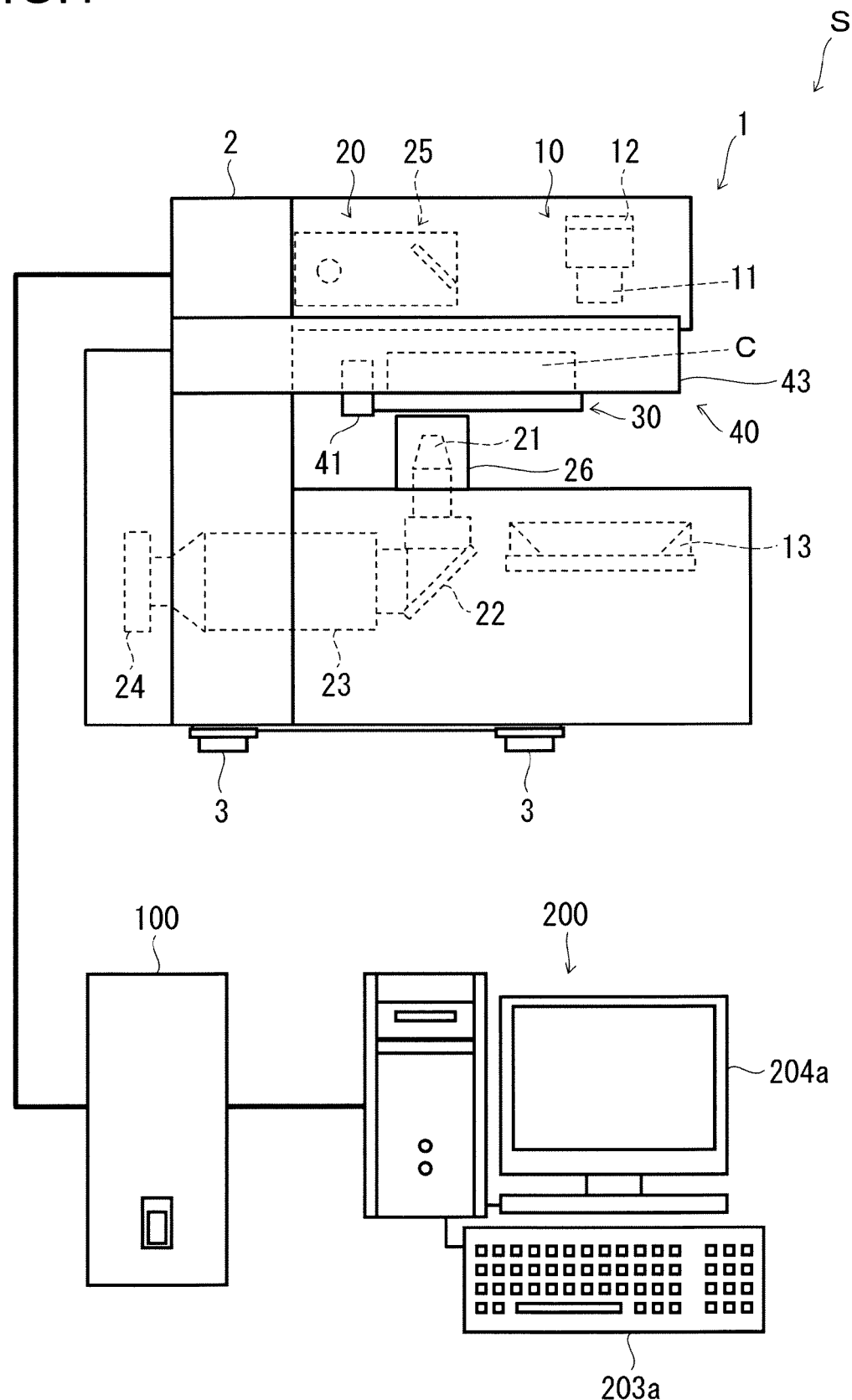
FIG. 1 is a configuration diagram of an observation system according to a first embodiment of the invention.
Figure 2:
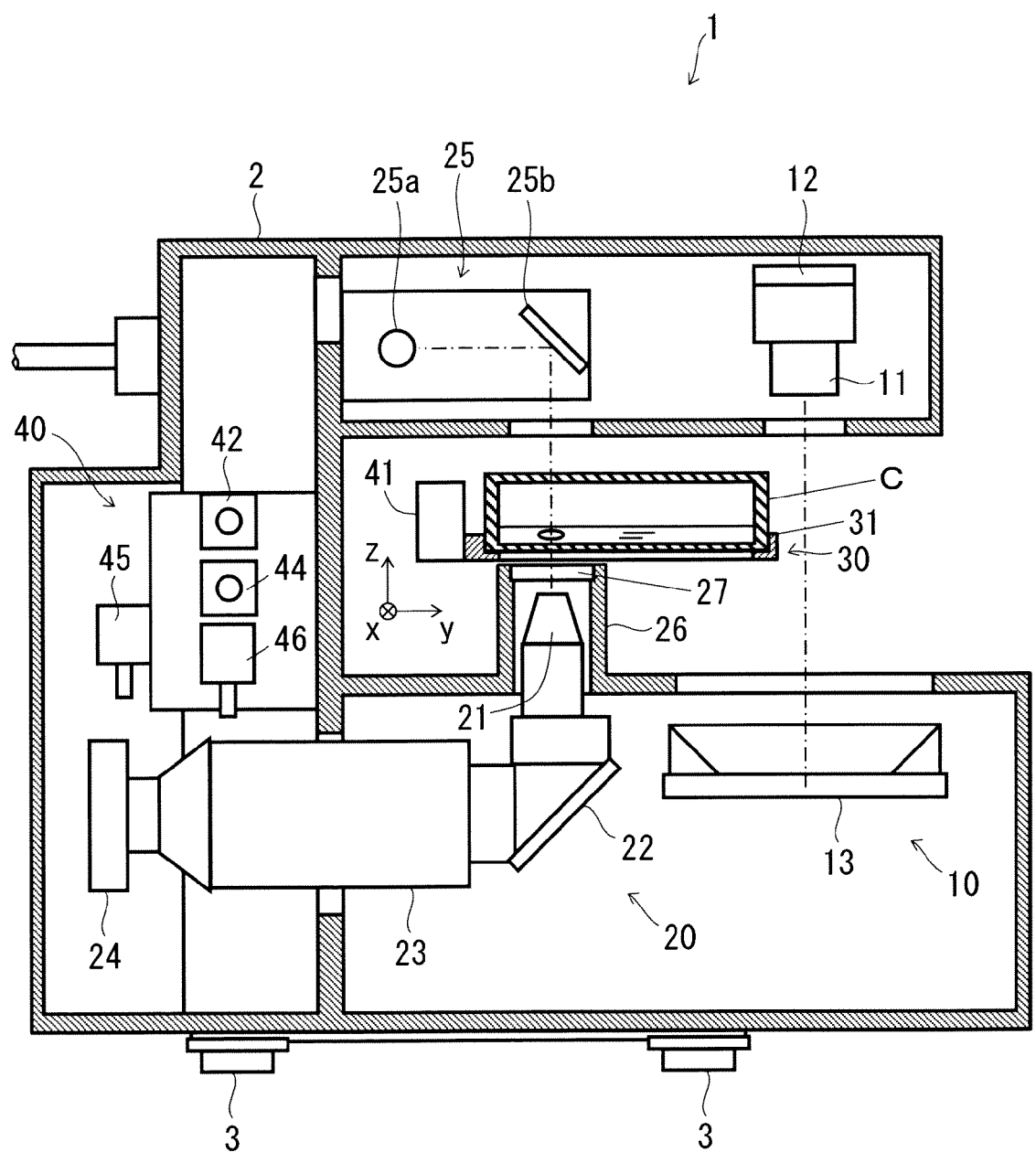
FIG. 2 is a vertical sectional side view of the observation device in the observation system shown in FIG. 1.
Figure 3:
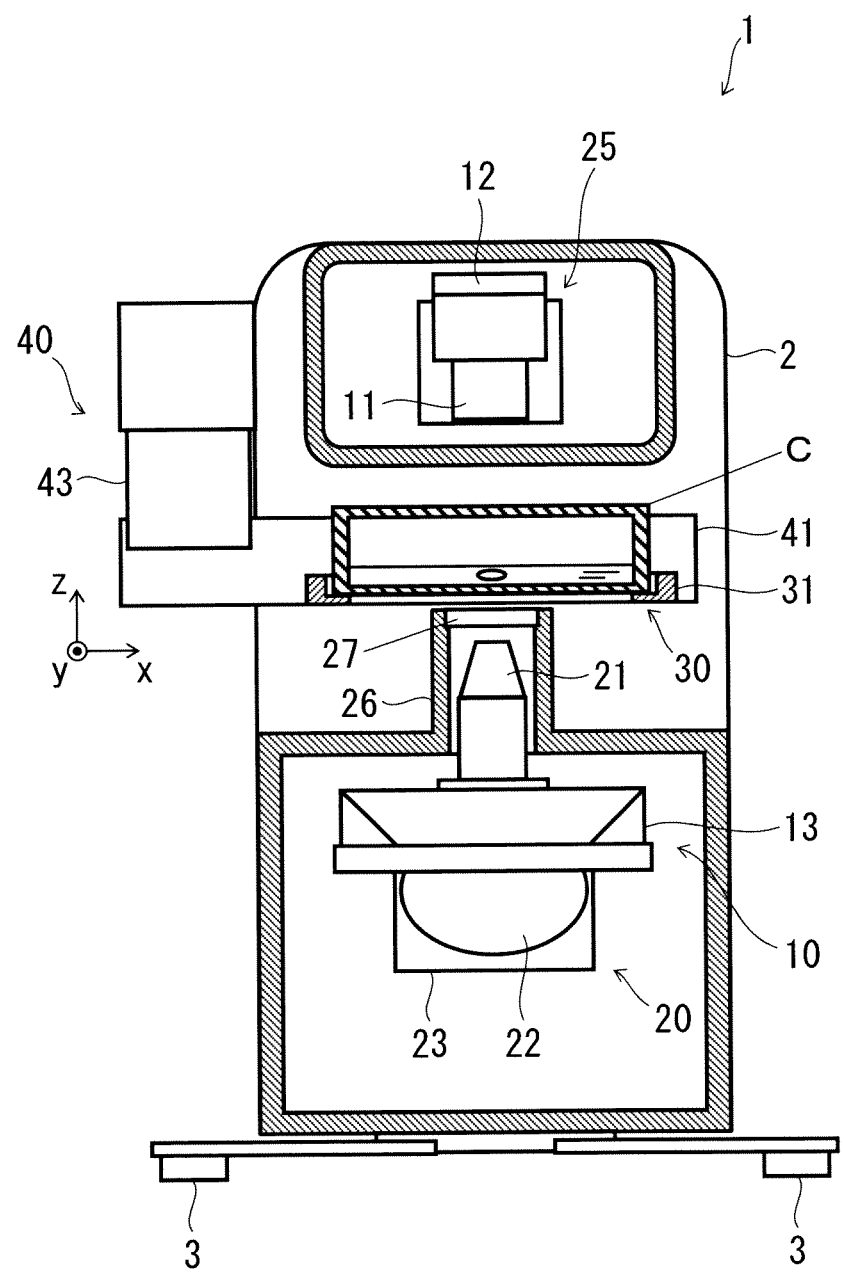
FIG. 3 is a vertical sectional front view of the observation device in the observation system shown in FIG. 1.
Figure 4:
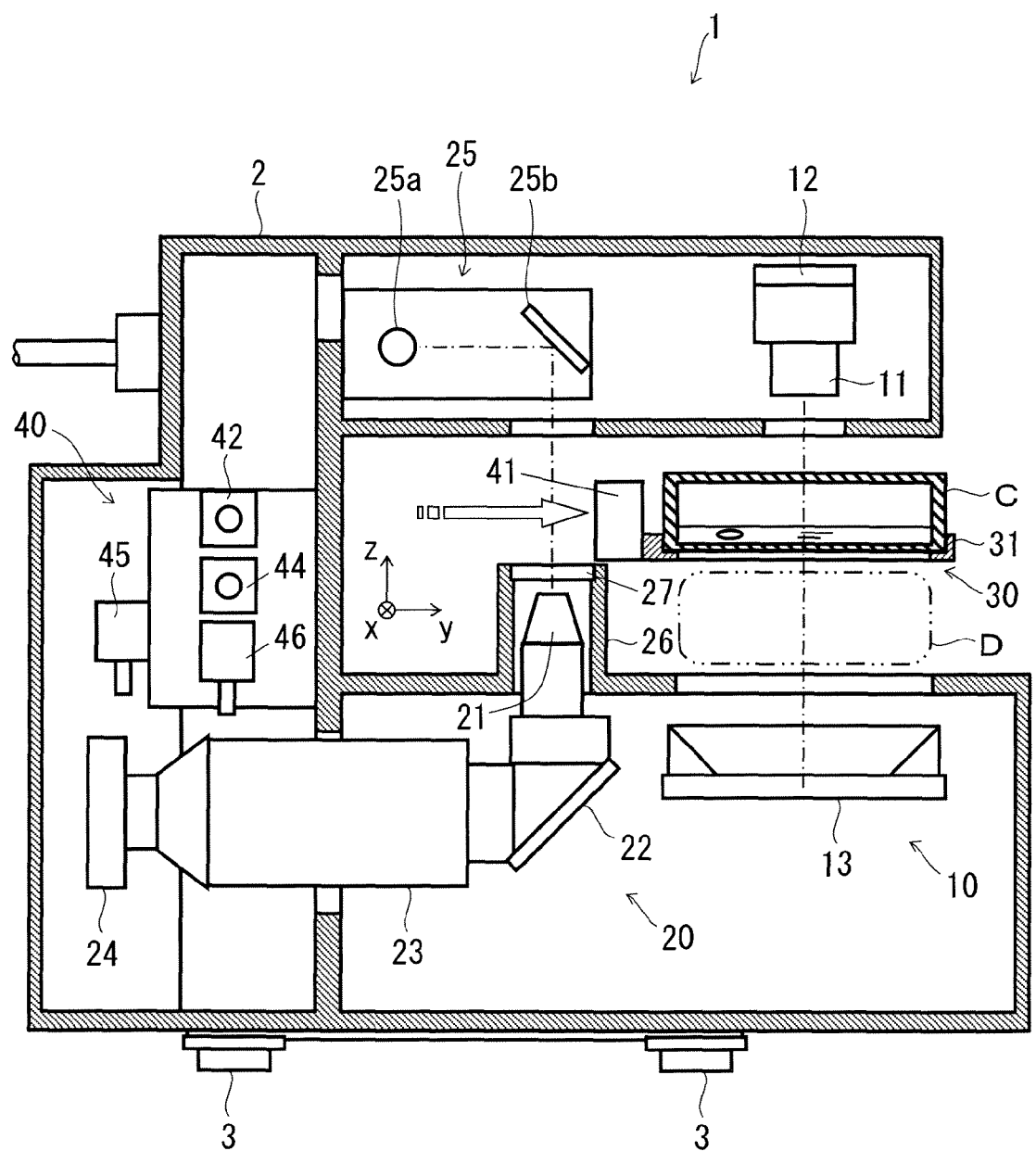
FIG. 4 is a vertical sectional side view similar to FIG. 2, showing a state in which the container has been moved to the position corresponding to the overall observation portion.
Figure 5:
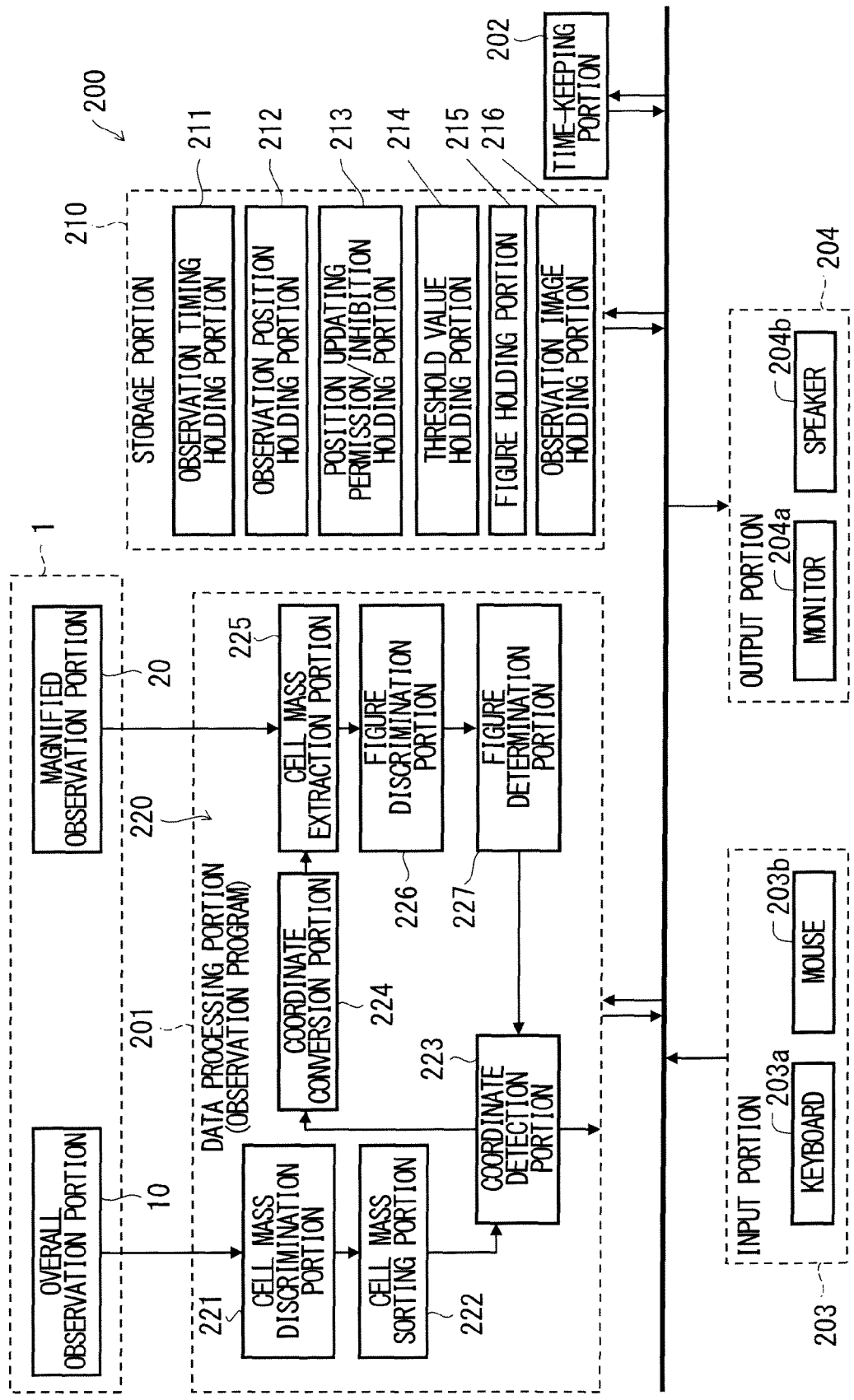
FIG. 5 is a block diagram showing the configuration of the computer in the observation system shown in FIG. 1.

First, the configuration of an observation system according to a first embodiment of the invention will be described with reference to FIGS. 1 to 5. FIG. 1 is a configuration diagram of the observation system. FIG. 2 is a vertical sectional side view of an observation device in the observation system. FIG. 3 is a vertical sectional front view of the observation device. FIG. 4 is a vertical sectional side view of the observation device, with a container moved to a position corresponding to an overall observation portion. FIG. 5 is a block diagram showing the computer configuration of the observation system. In the following description, the x-axis direction in FIGS. 2 and 3 is referred to as the left/right direction, the y-axis direction there is referred to as the front/rear direction (the +y side being frontward and the −y side being rearward), and the z-axis direction there is referred to as the up/down direction.

As shown in FIG. 1, the observation system S is provided with an observation device 1, a control device 100, and a computer 200.

The observation device 1 is a device for observation of a sample such as cells, and has the control device 100 connected to it. The control device 100 is a device for controlling the observation device 1, and incorporates a driver and a controller (of which none is illustrated) for operating the observation device 1. The control device 100 is connected to the computer 200. The computer 200 is, for example, a so-called personal computer, and executes an observation program (not illustrated) for observation of a sample such as cells. That is, the computer 200 can transmit commands to the control device 100 to control the observation device 1, and can perform acquisition and saving of images taken during observation.

As shown in FIGS. 1 to 4, the observation device 1 is provided with, inside its body 2 formed as a casing, an overall observation portion 10, a magnified observation portion 20, a transport portion 30, and a drive portion 40.

The observation device 1 allows, by use of the overall observation section 10 and the magnified observation section 20, observation of cells inside a container C which contains the cells and a culture fluid for them and which is placed in a front central part of the observation device 1. The drive portion 40 permits the transport portion 30, which holds the container C, to be moved in desired directions, namely in the front/rear and left/right directions, to the desired position. The body 2 is supported on a level surface by feet 3 which are provided at four places. The container C is fitted with a lid to prevent contamination from outside or from another container.

The overall observation portion 10 is provided in a front part inside the airtight casing of the body 2, and is provided with a lens 11 as an overall observation optical system, a CMOS camera 12 as an image sensing portion, and a ring illuminator 13 as an overall observation illuminator.

The lens 11 is arranged above the movement space of the transport portion 30, which holds the container C, and is provided so as to allow observation of the inside of the container C through downward viewing. The CMOS camera 12 is arranged vertically above the lens 11, and the image sensor surface of the CMOS camera 12 is arranged so as to point to the lens 11 below.

The ring illuminator 13 has a plurality of LEDs arranged in a ring-shaped formation, with the LEDs fitted so as to point obliquely upward, and is arranged below the movement space of the transport portion 30. Between the ring illuminator 13 and the container C on the transport portion 30, there is a gap D across a predetermined distance (see FIG. 4). Thus, between the ring illuminator 13 and the container C, a space is left through which air can pass, and this makes it difficult for the heat generated by the ring illuminator 13 to be conducted to the container C. It is thus possible to suppress the effect of the heat generated by the ring illuminator 13 on the growth of the cells. The ring illuminator 13 emits light obliquely upward, toward the center of the ring, and illuminates the observation target, that is, the cells inside the container C on the transport portion 30 located above the ring illuminator 13. The CMOS camera 12 and the lens 11 are arranged such that their respective optical axes coincide with each other, and the ring illuminator 13 is arranged such that the optical axis passes through its center.

In a part of the body 2 above the ring illuminator 13, an overall illumination window 14 is provided which is formed of glass or resin. The overall illumination window 14 is coated, or laid with a film, so as to function as a filter that transmits visible light from the ring illuminator 13 but cuts radiations of wavelengths in the ultraviolet and infrared ranges. Cutting ultraviolet radiation helps alleviate the damage that it inflicts on the cells, and cutting infrared radiation helps alleviate the unintended effect of heat that it inflicts on the container C. It is therefore preferable to cut at least either ultraviolet or infrared radiation.

As indicated by a double-headed arrow G in FIG. 2, the ring illuminator 13 is arranged with a gap (in this embodiment, a gap of about 2 mm) from the overall illumination window 14. This too makes it difficult for the heat of the ring illuminator 13 to be conducted via the casing or the overall illumination window 14 to the container C.

Configured as described above, the overall observation portion 10 shines light from the ring illuminator 13 on the container C, so that an image obtained through the lens 11 is focused on the CMOS camera 12; thus, through taking of an image of the entire container C, an image of the cells inside the container C is taken. The taken image is stored, and this makes it easy to discriminate and identify a cell mass, which a mass of a plurality of cell flocked together, inside the container C.

The overall observation portion 10 irradiates the container C with light from below obliquely upward. Thus, the light that passes through a part of the bottom face of the container C where cells are present is scattered by the cells, and part of the scattered light enters the camera, causing the cells to appear white. On the other hand, the light that passes through a part where no cells are present is not scattered, and no light enters the camera, causing the part to appear black. In this way, it is possible to shine light adequate to identify cells that occur and grow near the inner bottom face of the container C. It is then possible to obtain contrast sufficient to allow the exterior figure of the cells to be recognized as a white mass. Shining the light from below serves to prevent the cells from becoming unobservable by being saturated with the light reflected from the lid of the container C.

The magnified observation portion 20 is a so-called phase contrast microscope; it is provided in a part, behind the overall observation portion 10, inside the airtight casing forming the body 2, and is provided with a magnified observation optical system including an objective lens 21, a reflective mirror 22, and a zoom lens 23, a CCD camera 24 as an image sensing portion, and a phase contrast illuminating portion 25 as a magnified observation illuminator.

The objective lens 21 is arranged immediately below the movement space of the transport portion 30, and is provided so as to allow observation of the inside of the container C through upward viewing. Around the objective lens 21, which is a lens portion closest to the bottom face of the container C, an objective lens cover 26 is provided which is a cover member for preventing the heat generated in a lower part inside the body 2 below affecting the container C. At the upper tip end of the objective lens cover 26, between the objective lens 21 and the container C, a window 27 is provided.

Heat occurs and accumulates in the motor, camera, and illuminator inside the airtight casing, stagnates around the objective lens 21, and tends to dissipate upward. If, instead of the objective lens cover 26 with a comparatively small area, a cover that covers the entire magnified observation optical system is used, the closeness between the magnified observation optical system and the bottom face of the container C allows easy conduction of the heat inside the casing, making the temperature of the culture fluid more likely to rise.

By contrast, the objective lens cover 26, by minimizing the area over which it is close to the bottom face of the container C, helps suppress the effect of heat resulting from almost no gap being left between the bottom face of the container C and the objective lens cover 26 and hence no air passing there. At the same time, the objective lens cover 26, by covering only around the objective lens 21, can increase the surface area of the objective lens cover 26, and this makes it possible to dissipate heat also sideways with respect to the objective lens cover 26, where air passes easily, and thereby to suppress conduction of heat to the container C.

By, in this way, providing between the magnified observation optical system and the container C an objective lens cover 26 which covers only around the objective lens 21 and which has a window 27, it is possible to make it difficult for the heat generated by the magnified observation optical system to be conducted to the container C. It is thus possible to suppress the effect of the heat generated by the lens drive system on the growth of cells.

The reflective mirror 22 is arranged below the objective lens 21, and is provided with such an inclination as to reflect light rearward approximately in the horizontal direction. The reflective mirror 22 directs the image obtained from the objective lens 21 to the zoom lens 23 behind. The zoom lens 23 is arranged behind the reflective mirror 22 so as to extend in the front/rear direction, and magnifies the image obtained from the objective lens 21. The CCD camera 24 is provided further behind the zoom lens 23, and is arranged such that the image sensor surface of the CCD camera 24 points frontward, toward the zoom lens 23.

The phase contrast illuminating portion 25 is provided in an upper part of the body 2, and is provided with an LED 25a and a reflective mirror 25b. The LED 25a emits light with which to illuminate the observation target, that is, the cells inside the container C on the transport portion 30 located below the phase contrast illuminating portion 25. The reflective mirror 25b is arranged vertically above the objective lens 21, and reflects the light emitted from the LED 25a so that it travels through the container C and reaches the objective lens 21.

Configured as described above, the magnified observation portion 20 shines light from the phase contrast illuminating portion 25 on the container C, so that an image obtained via the objective lens 21, the reflective mirror 22, and the zoom lens 23 is focused on the image sensor surface in the CCD camera 24; thus, a partial region within the container C is magnified, and an image of cells inside the container C is taken. The taken image is then stored, and this makes it easy to discriminate and identify, and closely observe, a cell mass inside the container C.

In the magnified observation portion 20, the magnified observation optical system, which is comparatively heavy by including a plurality of lenses and a zoom mechanism for them for magnified observation of cells, is arranged in a lower part, and this gives the device a proper weight balance and thereby allows stable magnified observation. Moreover, the objective lens 21 can be brought close to cells that occur and grow near the inner bottom face of the container C from below the container C, and this makes it possible to shorten the focal length to allow observation at a comparatively high magnification. Moreover, since the magnified observation portion 20 allows observation through viewing from below the container C, it is possible to perform observation without being affected by stain on the lid of the container C.

The transport portion 30 is provided in a front central part of the body 2, so as to be located between, at the lower side, the ring illuminator 13 of the overall observation portion 10 and the magnified observation optical system of the magnified observation portion 20 and, at the upper side, the overall observation optical system of the overall observation portion 10 and the phase contrast illuminating portion 25 of the magnified observation portion 20. The transport portion 30 is provided with a holder 31, and this holder 31 holds the container C containing cells as the observation target and a culture fluid for them. The holder 31 is positioned with respect to the overall observation portion 10 and the magnified observation portion 20, and the container C is positioned with respect to the holder 31. Thus, even when the container C is removed along with the holder 31 for replacement of the culture fluid or for addition of a chemical, it is easy to observe the same location in the overall observation portion 10 and the magnified observation portion 20.

The drive portion 40 is provided at the back and side of the transport portion 30, and is provided with an x-axis drive mechanism 41, an x-axis motor 42, a y-axis drive mechanism 43, a y-axis motor 44, a z-axis motor 45, and a zoom motor 46. The following description proceeds assuming that, as shown in FIGS. 2 and 3, the left/right, front/rear, and up/down directions with respect to the observation device 1 are the x, y, and z axes respectively.

The x-axis drive mechanism 41 is arranged immediately behind the transport portion 30, and directly supports the transport portion 30. The x-axis drive mechanism 41 is provided with a belt, a pulley, a slide guide member, and a shaft (of which none is illustrated), and is driven by the x-axis motor 42 to make the transport portion 30 move in the left/right direction. The y-axis drive mechanism 43 is arranged in a side part of the transport portion 30 and of the body 2, and supports the x-axis drive mechanism 41. The y-axis drive mechanism 43 is provided with a belt, a pulley, and a slide guide member (of which none is illustrated), and is driven by the y-axis motor 44 to make the transport portion 30, along with the x-axis drive mechanism 41, move in the front/rear direction (see FIG. 4).

By operating the drive mechanism described above, the transport portion 30 transports the container C from the overall observation portion 10 to the magnified observation portion 20 and in the reverse direction. Since the container C is movable, even when the overall observation portion 10 and the magnified observation portion 20 are located away from each other, it is possible to observe the entire container C and identify a cell mass that has occurred, and in addition to magnify the identified cell mass and observe its details.

As described above, the transport portion 30 transports the container C in directions perpendicular to the optical axes of the overall observation portion 10 and the magnified observation portion 20, and at least one of the transport directions, namely the front/rear direction, is common so that coordinates within the observation view field in the overall observation portion 10 coincide with coordinates within the observation view field in the magnified observation portion 20. Thus, coordinates within the observation view field coincide between the overall observation portion 10 and the magnified observation portion 20, and this permits a cell mass identified through observation of the entire container C in the overall observation portion 10 to be easily discriminated in the magnified observation portion 20. This helps prevent erroneous discrimination of a target cell mass and thus allows observation with high precision.

The z-axis motor 45 and the zoom motor 46 are arranged inside the body 2, behind the transport portion 30. The z-axis motor 45 is a motor for moving the magnified observation optical system and the CCD camera 24 in the up/down direction. The zoom motor 46 is a motor for varying the magnification of the zoom lens 23, and allows the magnification of taken images to be varied As shown in FIG. 5, the computer 200 is provided with at least a data processing portion 201, and may be further provided with a storage portion 210, a time keeping portion 202, an input portion 203, and an output portion 204.

The data processing portion 201 comprises a common microcomputer and other electronic components, and controls a series of observation operations that proceeds in the observation device 1 based on an observation program 220 and data stored in the microcomputer itself, stored in the storage portion 210, or fed from outside. An image processing portion for processing the image taken by the overall observation portion 10 or the magnified observation portion 20 may be provided separately.

As shown in a functional block diagram on a hardware basis in FIG. 5, the observation program 220 executed by the data processing portion 201 is provided with a cell mass discrimination portion 221, a cell mass sorting portion 222, a coordinate detection portion 223, a coordinate conversion portion 224, a cell mass extraction portion 225, a figure discrimination portion 226, and a figure determination portion 227. In addition to these processing blocks, the observation program 220 executes overall image sensing processing, in which it instructs the overall observation portion 10 of the observation device 1 to take an image of the entire container C and thereby take an image of cells, and magnified image sensing processing, in which it instructs the magnified observation portion 20 to magnify part of the inside of the container C and take an image of cells.

The cell mass discrimination portion 221, first, if the target is a color image, coverts it into a gray image, and then distinguishes between, of the image taken in the overall image sensing processing, a part not corresponding to a cell mass and a part corresponding to a cell mass by use of a predetermined threshold value. This achieves binarization, making the non-cell-mass part black and the cell-mass part white. Then, the cell mass discrimination section 221 calculates the number of cells, that is, the number of white pixels. The method of calculating the number of white pixels here is, for example, a labeling method whereby connected regions of whit pixels are calculated, or a small area method whereby regions are calculated such as to maximize the number of white pixels within a predetermined small area at an arbitrary position.

The labeling method is a method whereby a cell mass is discriminated based on the sizes of single white pixel regions and the degree of density of white pixel regions, and the small area method is a method whereby a cell mass is discriminated based on the number, the quantity, and the degree of density of white pixel regions. Other than these, it is also possible to achieve discrimination based on the degree of isolation of cell masses (the degree of how individual cell masses are located at predetermined distances from one another). Here, it is assumed that the labeling method is used.

Labeling processing denotes processing whereby, with respect to an image having undergone binarization processing, any neighboring white pixels (or black pixels) are assigned the same number (label) for the purpose of classifying a plurality of pixels into groups. In labeling processing, neighborhood is determined on the principle of four-neighbor connectivity (four neighbors) and eight-neighbor connectivity (eight neighbors). In four-neighbor connectivity, abutting a pixel of interest from four sides—top, bottom, left, and right—is determined as neighboring it; in eight-neighbor connectivity, abutting it additionally from four diagonal directions is determined as neighboring. In this way, the cell mass discrimination portion 221 discriminates, from the image taken in the overall image sensing processing, a mass of binarized white pixels, that is, a cell mass.

The cell mass discrimination portion 221 recognizes, of cell masses so discriminated, any with a larger than a predetermined size as an observation target cell mass. The "predetermined size" is a previously set size of a cell mass, and is such a size as to permit a decision to take it as a magnified observation target. Here, the predetermined size is set at, for example, in terms of the number of pixels, 1000 pixels, and is stored in the storage portion 210. Thus, a cell mass equivalent, in terms of the number of pixels, to 1000 pixels or more is recognized as a magnified observation target cell mass, and this makes it possible to grasp the time of occurrence of the cell mass. Thus, it is possible to perform continuous observation from the occurrence of a cell mass till the completion of its growth.

The cell mass sorting portion 222 sorts cell masses discriminated by the cell mass discrimination portion 221, that is, masses of white pixels, in order of decreasing numbers of pixels. Then, for example, a previously set number of cell masses in order of decreasing numbers of pixels starting with the one with the greatest number are selected as observation targets.

The coordinate detection portion 223 detects the center coordinates of the cell masses discriminated by the cell mass discrimination portion 221 and then sorted by the cell mass sorting portion 222, that is, the center coordinates of the masses of white pixels.

The coordinate conversion portion 224 first calculates coordinates on the basis of the pixels on the image taken in the overall image sensing processing; it then converts them into actual dimensions with the origin at the center of the image. Here, different kinds of aberration, such as distortion, of the image may be corrected. The coordinate conversion portion 224 further converts the actual dimensions into the numbers of motor pulses for the x-axis and y-axis motors 42 and 44 in the drive portion 40 so that these match the position on the image as represented by the actual dimensions. In this way, the coordinate conversion portion 224 forms a common coordinate system in which coordinates on the image taken in the magnified image sensing processing coincide with coordinates on the image taken in the overall image sensing processing.

The cell mass extraction portion 225 extracts from the image taken in the magnified image sensing processing the cell masses at the coordinates detected by the coordinate detection portion 223.

The figure discrimination portion 226 first performs matching on the image taken in the magnified image sensing processing with a previously prepared patch image. As a result of the matching, a range image is obtained in which the difference between the image taken in the magnified image sensing processing and the patch image is expressed in varying densities. The figure discrimination portion 226 then performs binarization processing on the range image by use of a predetermined threshold value. The method of matching here is, for example, template matching or histogram matching; the determination target image, that is, the image taken in the magnified image sensing processing, is raster-scanned with the patch image to calculate the distance between those images. In a case where a number of patch images are prepared, the range images resulting from the matching are accumulated. Even when a plurality of cell masses are present within the image taken in the magnified image sensing processing, the figure discrimination portion 226 can discriminate them as separate ones.

Subsequently, the figure discrimination portion 226 performs on the image having undergone binarization processing, for example, edge extraction with an edge extraction filter and contour tracing by eight-neighbor search to detect a contour. Usable as the edge extraction filter in contour extraction is, for example, a differential filter, a Prewitt filter, a Sobel filter, or a Canny edge detector. In contour tracing, a contour line can be extracted by sequentially extracting contour points in one direction from a contour tracing start point, and four-neighbor search may instead be used.

The figure discrimination portion 226 detects from the results of the contour detection a predetermined figure such as a circle, ellipse, or rectangular. Usable as a method of detecting a circle from a contour or edge is, for example, the Hough transform. Usable as a method of detecting an ellipse from a contour or edge is, for example, a method whereby an ellipse is fitted to a series of points on a contour by the generalized Hough transform or by least squares evaluation. Usable as a method of detecting a rectangular from a contour or edge is, for example, a method whereby a rectangular is so fitted as to include an entire series of points on a contour. In this way, the figure discrimination portion 226 extracts the contour of a cell mass from the image taken in the magnified image sensing processing and discriminates a figure.

The figure determination portion 227 checks whether or not the figure of the cell mass discriminated by the figure discrimination portion 226 is a predetermined figure. The "predetermined figure" is a previously set figure of a cell mass, and is such a figure as to permit a judgment that it is likely to continue growing in a way adequate for observation; preferably, it is as close to circular as possible.

In checking whether or not a cell mass has a predetermined figure, other conditions may additionally be considered, for example, the size, and the degree of concavity or convexity. Examples of conditions for determination of a figure include the ellipticity of an ellipse surrounding a contour, and the roundness of a circle surrounding a contour. Examples of conditions for determination of a size include the size of a white pixel mass, the length of the contour of a white pixel mass, the area inside the contour of a white pixel mass, the major axis length of an ellipse, the minor axis length of an ellipse, the circumferential length of an ellipse, the diameter of a circle, the circumferential length of a circle, the length of the rectangular surrounding a contour, and the area of the rectangular surrounding a contour. Examples of conditions for determination of the degree of concavity or convexity include the ratio of the area of a contour to its circumferential length, the ratio of the area of a contour to the area of the rectangular surrounding it, the ratio of the length of a contour to the length of the rectangular surrounding it, the number of corners in a contour, the ratio of the area of a contour to the area of a circle or ellipse surrounding it, the ratio of the length of a contour to the circumferential length of a circle or ellipse surrounding it, the ratio of the area of the rectangular surrounding a contour to the area of the circle or ellipse surrounding it, the ratio of the length of the rectangular surrounding a contour to the length of a circle or ellipse surrounding it. The method of detecting corners in a case where determination is made based on the number of corners in a contour is, for example, the Harris corner detection, and the SUSAN operator.

Here, it is assumed that the condition for checking whether a cell mass has a predetermined figure is, for example, an ellipticity of 1.1 or less, and this is stored in the storage portion 210. Ellipticity is the ratio of the major axis length of an ellipse to its minor axis length. It may instead be the value given by "$4\pi \times $(area inside contour)/(length of contour)$^2$."

This permits discrimination of a cell mass as close to circular as possible, and thus allows automatic selection of cell masses having figures adequate for continued observation. Thus, it is possible to give lower priority to, or stop, observation of cell masses that have grown to have distorted figures, and thus it is possible to proceed with observation of cell masses having adequate figures more efficiently.

Instead of a method whereby determination of a figure is made explicitly on the basis of a threshold value (for example, an ellipticity of 1.1), it is also possible to adopt a method whereby cell mass images are sorted according to whether their determination results are good or bad and displayed on a monitor 204a (when ellipticity is the criterion, displayed in increasing order of ellipticity) and determination of up to what position they are suitable is delegated to the user.

The storage portion 210 is for storing various kinds of data related to the observation of cells and the operation of the observation system S, and is provided with, for example, an observation timing holding portion 211, an observation position holding portion 212, a position updating permission/inhibition holding portion 213, a threshold value holding portion 214, a figure holding portion 215, and an observation image holding portion 216.

The observation timing holding portion 211 holds various items of data related to time and date, such as the period, the number of days, and the deadline associated with observation. The data includes, for example, a "predetermined discrimination period," which is a predetermined period related to discrimination of cell masses and which defines the timing with which to execute discrimination of magnified observation target cell masses; a "predetermined number of discrimination days," which defines the timing with which to end discrimination of magnified observation target cell masses; a "predetermined image sensing period," which is a predetermined period related to taking of magnified images and which defines the timing with which to execute magnified image sensing of cell masses; and a "predetermined observation deadline," which is a previously set predetermined deadline with respect to the timing with which to end observation of cells. These items of data are used as conditions for determination as necessary in the observation program 220, and are compared with the date and time counted by the time keeping portion 202.

The observation position holding portion 212 holds data such as cell mass observation positions (coordinates) obtained in overall observation, and observation positions (coordinates) set manually.

The position updating permission/inhibition holding portion 213 holds a flag indicating whether or not to update the cell mass observation positions that have been obtained in the previous overall observation and stored in the observation position holding portion 212 according to the predetermined discrimination period stored in the observation timing holding portion 211.

The threshold value holding portion 214 holds various items of data related to threshold values in connection with observation. The data includes, for example, a threshold value for checking whether a pixel is white or black in binarization processing, and a threshold value related to the number of pixels for checking whether or not to extract a labeled mass of white pixels as a cell mass.

The threshold value holding portion 214 holds, when figure discrimination processing is executed, threshold values for discriminating cell masses that are likely to grow properly. It holds data such as a threshold value for the number of pixels for determination based on the size of white pixel masses; a threshold value for the length of a contour for determination based on the length of the contour of white pixel masses; a threshold value for an area for determination based on the area inside the contour of white pixel masses; a threshold value for roundness for determination based on the roundness of the circle surrounding a contour; a threshold value for the ratio of the major axis length of an ellipse to its minor axis length for determination based on the ellipticity of an ellipse surrounding a contour; a threshold value for a diameter for determination based on the diameter of a circle; a threshold value for a circumferential length for determination based on the circumferential length of a circle; a threshold value for a major axis length for determination based on the major axis length of an ellipse; a threshold value for a minor axis length for determination based on the minor axis length of an ellipse; a threshold value for the circumferential length of an ellipse for determination based on the circumferential length of an ellipse; a threshold value for the length of a rectangular for determination based on the length of the rectangular surrounding a contour; a threshold value for the area of a rectangular for determination based on the area of the rectangular surrounding a contour; a threshold value for the ratio of the area of a contour and its circumferential length for determination based on the ratio of the area of a contour and its circumferential length; a threshold value for a ratio of areas for determination based on the ratio between the area of a contour and the area of the rectangular surrounding it; a threshold value for a ratio of lengths for determination based on the ratio of the length of a contour and the length of the rectangular surrounding the contour; a threshold value for the number of corners for determination based on the number of corners in a contour; a threshold value for a ratio of areas for determination based on the ratio of the area of a contour and the area of the circle or ellipse surrounding it; a threshold value for a ratio of lengths for determination based on the ratio of the length of a contour and the length of the circle or ellipse surrounding it; a threshold value for a ratio of areas for determination based on the ratio of the area of the rectangular surrounding a contour and the area of an circle or ellipse surrounding it; and a threshold value for a ratio of lengths for determination based on the ratio of the length of the rectangular surrounding a contour and the length of the circle or ellipse surrounding it.

The figure holding portion 215 holds, with respect to every method for figure discrimination processing, the results of the figure discrimination processing on cell masses.

The observation image holding portion 216 holds magnified observation images and overall observation images.

The observation timing holding portion 211 and the threshold value holding portion 214 each also function as a setting portion that allows the user to modify, as necessary, various settings related to the observation program 220. The settings that can be modified via the observation timing holding portion 211 are, for example, those on the timing with which to take images in the overall observation portion 10 and the magnified observation portion 20, and the period, the number of days, and the deadline associated with observation. The settings that can be modified via the threshold value holding portion 214 are, for example, those on the predetermined size of a cell mass for determination of whether it is a magnified observation target cell mass, and the predetermined figure of a cell mass for determination of whether its figure is adequate for continued observation.

The time keeping portion 202 counts days and hours from the start of observation of cells and time related to the control of the operation of the observation system S, and allows a grasp of different flows of time The input portion 203 comprises, for example, a keyboard 203a and a pointing device such as a mouse 203b. Using the keyboard 203a, the user enters characters and values. Using the mouse 203b, the user moves a cursor in desired directions across the screen of a monitor 204a in the output portion 204 to select menus and make other choices. According to information fed in through the input portion 203, the data processing portion 201 executes various kinds of processing on programs, data, and files stored in or entered to the data processing portion 201 and the storage portion 210, and executes output processing for the output portion 204.

The output portion 204 comprises, for example, a monitor 204a such as a liquid crystal display or a CRT and a speaker 204b. According to the processing performed as the program is executed, the data processing portion 201 makes the monitor 204a display windows, icons, and menus, and makes the speaker 204b reproduce sound. According to information from the input portion 203, the data processing portion 201 makes the monitor 204a display the characters, values, etc. entered by the user and the cursor which the user moves.

Figure 6:
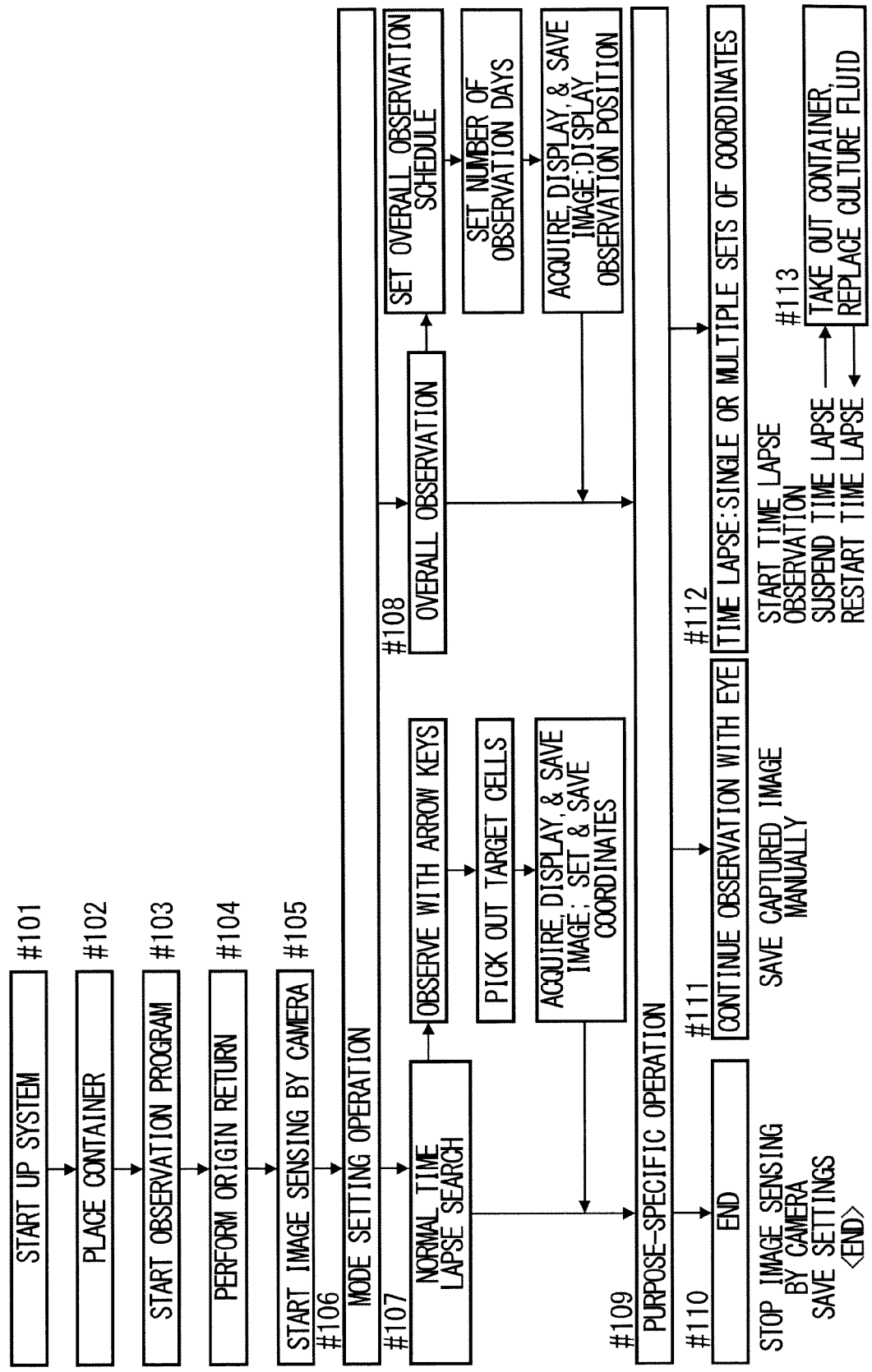
FIG. 6 is a diagram in illustration of the flow related to the operation of the observation system of FIG. 1.

Now, a description will be given of the operation of the observation system S by the user for and during observation of cells inside the container C along the flow shown in FIG. 6. FIG. 6 is a diagram illustrating a flow of the operation of the observation system S.

First, the user turns on the power to the observation device 1, the control device 100, and the computer 200 to start up the observation system S (Step #101 in FIG. 6). Then, the user places on the holder 31 of the transport portion 30 a container C containing cells and a culture fluid for them (Step #102). Subsequently, the user starts the observation program 220 on the computer 200 (Step #103), and this causes an operation screen to appear on the monitor 204a.

In a fashion coordinated with its start, the observation program 220 automatically makes the transport portion 30 perform an origin return operation (Step #104). The observation program 220 then starts image sensing with the camera (Step #105), and make the monitor 204a display the real time image from the camera.

Subsequently, the user makes a mode setting operation (Step #106). The mode setting operation allows choice between a normal time lapse search operation (Step #107) and an overall observation operation (Step #108). A time lapse observation is a method whereby observation is performed at a previously set position every predetermined period.

In the normal time lapse search operation (Step #107), the user observes the inside of the container C while moving it by using arrow keys on the monitor 204a or on the keyboard 203a to locate target cells. The user then executes acquisition, display, and saving of captured images and setting and saving of coordinates.

In the overall observation operation (Step #108), the user sets the predetermined discrimination period and the predetermined number of discrimination days in overall observation. Acquisition, display, and saving of images and display of observation positions are executed automatically according to the settings.

Next, a purpose-specific operation (Step #109) allows choice among "end" (Step #110), "continue eye observation" (Step #111), and "time lapse" (Step #112).

When "end" (Step #110) is selected the image sensing by the camera is stopped, and the settings are saved. When "continue eye observation" is selected, a capture image taken by the camera can be saved manually.

When "time lapse" (Step #112) is selected, further choice is allowed among "start time lapse observation," "suspend time lapse," and "restart time lapse." When time lapse is suspended, it is possible to perform operations such as removing the container C and replacing the culture fluid (Step #113).

Through time lapse observation using the observation program 220 described above, it is possible to automatically perform a sequence of operations involving discriminating from an image taken in overall image sensing processing cell masses that have occurred, identifying their positions, then discriminating from an image taken in magnified image sensing processing the figures of cell masses, and selecting cell masses that have figures adequate for continued observation.

Figure 7:
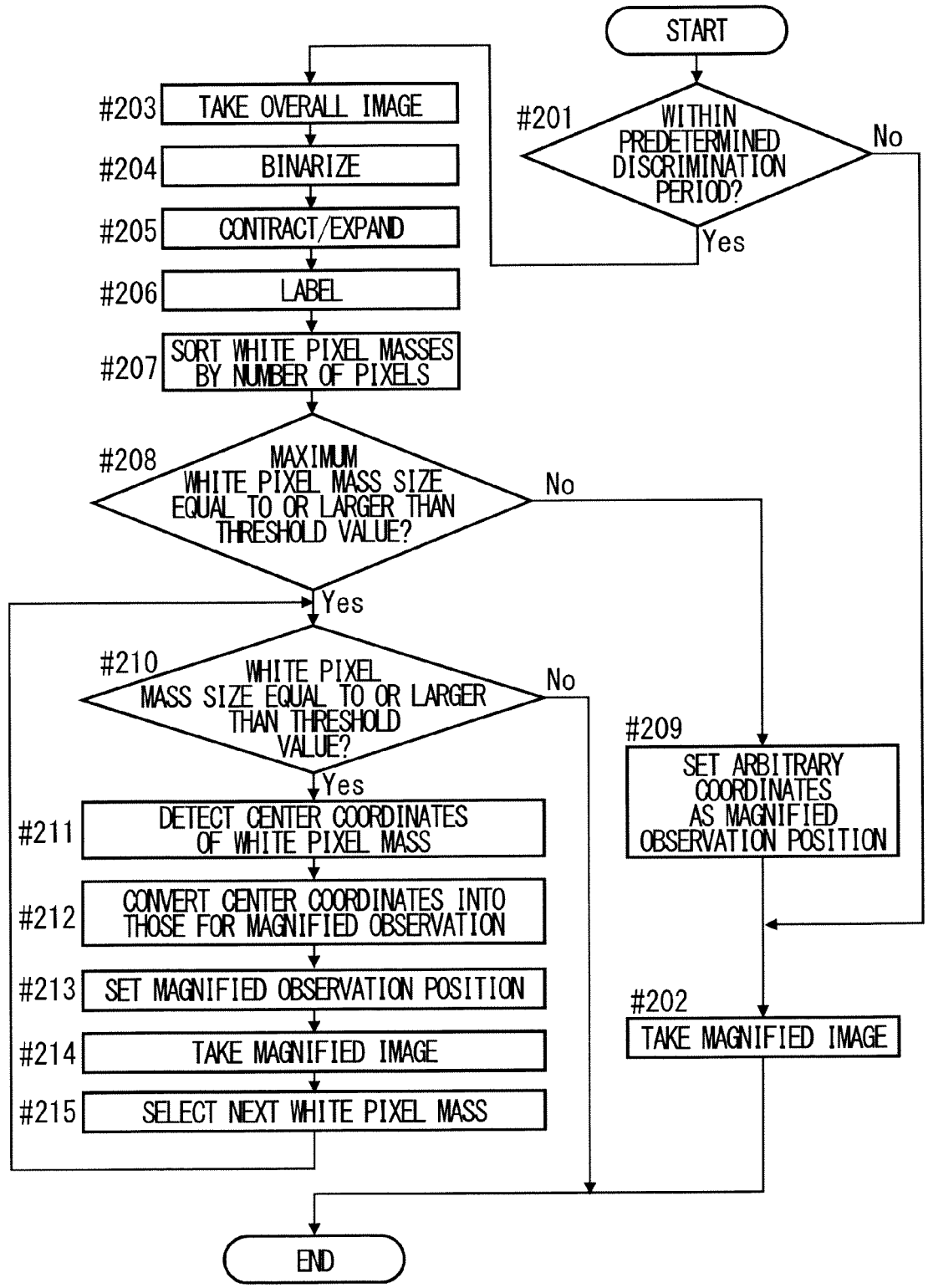
FIG. 7 is a flow chart showing the operation of observation processing in the observation system of FIG. 1.

Next, a description will be given of operations related to observation processing in the observation system S along the flow shown in FIG. 7. FIG. 7 is a flow chart showing operations related to observation processing in the observation system S.

When the observation program 220 is executed ("START" in FIG. 7), the observation program 220 first checks whether or not now is within the predetermined discrimination period (Step #201). In this connection, the observation program 220 has previously made the time keeping portion 202 count the days and hours after semination, for example from the start of observation of cells, and the period after the previous discrimination of magnified observation target cell masses in the magnified observation portion 20. The predetermined discrimination period is a previously set period with respect to the timing with which to execute discrimination of magnified observation target cell masses, is set at, for example, one day, and is stored in the observation timing holding portion 211 in the storage portion 210. The predetermined discrimination period can be set as desired.

If, at step #201, now is not within the predetermined discrimination period ("No" at Step #201), the observation program 220 makes the magnified observation portion 20 take a magnified image (Step #202), and ends the flow of the sequence of operations related to observation ("END" in FIG. 7).

On the other hand, if, at Step #201, now is within the predetermined discrimination period ("Yes" in Step #201), the observation program 220 instructs the overall observation portion 10 in the observation device 1 to sense the entire container C to take an image of cells (Step #203). Next, the observation program 220 executes binarization processing to distinguish between, of the overall image taken, a part not corresponding to a cell mass and a part corresponding to a cell mass by use of a predetermined threshold value (Step #204). This achieves binarization, making the non-cell-mass part black and the cell-mass part white.

Furthermore, the observation program 220 executes contraction/expansion processing (Step #205). Contraction/expansion processing includes contraction processing, whereby white pixels abutting black pixels are stripped off, and expansion processing whereby, to the contrary, white pixels abutting black pixels are added. In contraction processing, minute masses of white pixels are reversed to black pixels; in expansion processing minute masses of black pixels present in a region of white pixels are reversed to white pixels. Thus, both contributes to noise elimination.

The observation program 220 then executes labeling processing (Step #206); that is, it calculates the number of white pixels for each predetermined small region at an arbitrary position to discriminate masses of white pixels, that is, cell masses. Furthermore, the observation program 220 sorts the discriminated cell masses, that is, white pixel masses, in order of decreasing numbers of pixels starting with the one with the greatest number (Step #207).

Next, the observation program 220 checks whether or not the largest white pixel mass (cell mass) has a size equal to or larger than a threshold value, that is, the predetermined size (Step #208). The predetermined size as the threshold value here is set, for example, in terms of the number of pixels, at 1000 pixels, and is stored in the threshold value holding portion 214 in the storage portion 210. If the largest cell mass has a size smaller than the predetermined size ("No" in Step #208), the observation program 220 detects arbitrary coordinates in the overall image taken by the overall observation portion 10 and sets them as the magnified observation position (Step #209), and makes the magnified observation portion 20 take a magnified image (Step #202). Then, the observation program 220 ends the flow of the sequence of operations related to observation processing ("END" in FIG. 7).

On the other hand, if, at Step #208, the largest cell mass has a size equal to or larger than the predetermined size ("Yes" at Step #208), the observation program 220 checks again whether or not the selected cell mass has a size equal to or larger than the predetermined size (Step #210). If the cell mass has a size equal to or larger than the predetermined size ("Yes" at Step #210), the observation program 220 recognizes the white pixel mass (cell mass) as a magnified observation target cell mass and detects its center coordinates (Step #211). Furthermore, the observation program 220 converts those center coordinates into those for magnified image observation (Step #212).

Next, the observation program 220 sets the converted center coordinates of the cell mass as a magnified observation position (Step #213), and makes the magnified observation portion 20 take a magnified image (Step #214). Then, the observation program 220 selects the next white pixel mass (cell mass) as the target of the check of whether or not it is a magnified observation target cell mass (Step #215), and then returns to Step #210 to check whether or not the selected cell mass has a size equal to or larger than the predetermined size.

Until the cell mass discriminated at Step #206 is found to have a size smaller than the predetermined size ("No" at Step #210), the flow from Step #210 through Step #215 is repeated to continue to set the magnified observation position of cell masses discriminated as magnified observation targets. When the cell mass discriminated at Step #206 is found to have a size smaller than the predetermined size ("No" at Step #210), the observation program 220 ends the flow of the sequence of operations related to observation processing ("END" in FIG. 7).

In time lapse observation, either the position of the cell mass to be taken as a magnified observation target is set manually by the user, or the setting (identifying) of the position of the cell mass is done based on the overall observation results. With respect to the cell mass whose position has been identified, the observation program 220 instructs, every predetermined image sensing period, the magnified observation portion 20 to magnify the inside of the container C and take an image of cells there, until ending the image sensing on condition that the predetermined observation deadline has been reached.

The predetermined observation deadline is a deadline that has previously been set with respect to the timing with which to end observation of cells, is set at, for example, 10 days, and is sored in the observation timing holding portion 211. The predetermined observation deadline can be set as desired.

In this way, from an image resulting from sensing the entire container C, cell masses are discriminated, their coordinates are detected, and they are magnified about the detected coordinates to allow close observation of those cell masses. Moreover, magnified images of cells are taken every predetermined image sensing period until the image sensing is ended when the observation deadline is reached, and this allows continuous time lapse observation from occurrence of cell masses till completion of their growth.

According to this embodiment of the invention, it is possible to provide an observation device 1 that, in observation of cells being cultured inside a container C, allows observation of the entire container C for identification of cell masses having occurred and in addition allows magnification of the identified cell masses for observation of their details. It is also possible to provide an observation program 220, an observation method, and an observation system S that allow continuous observation of the identified cell masses from their occurrence till the completion of their growth.

(Embodiment 2)

Figure 8:
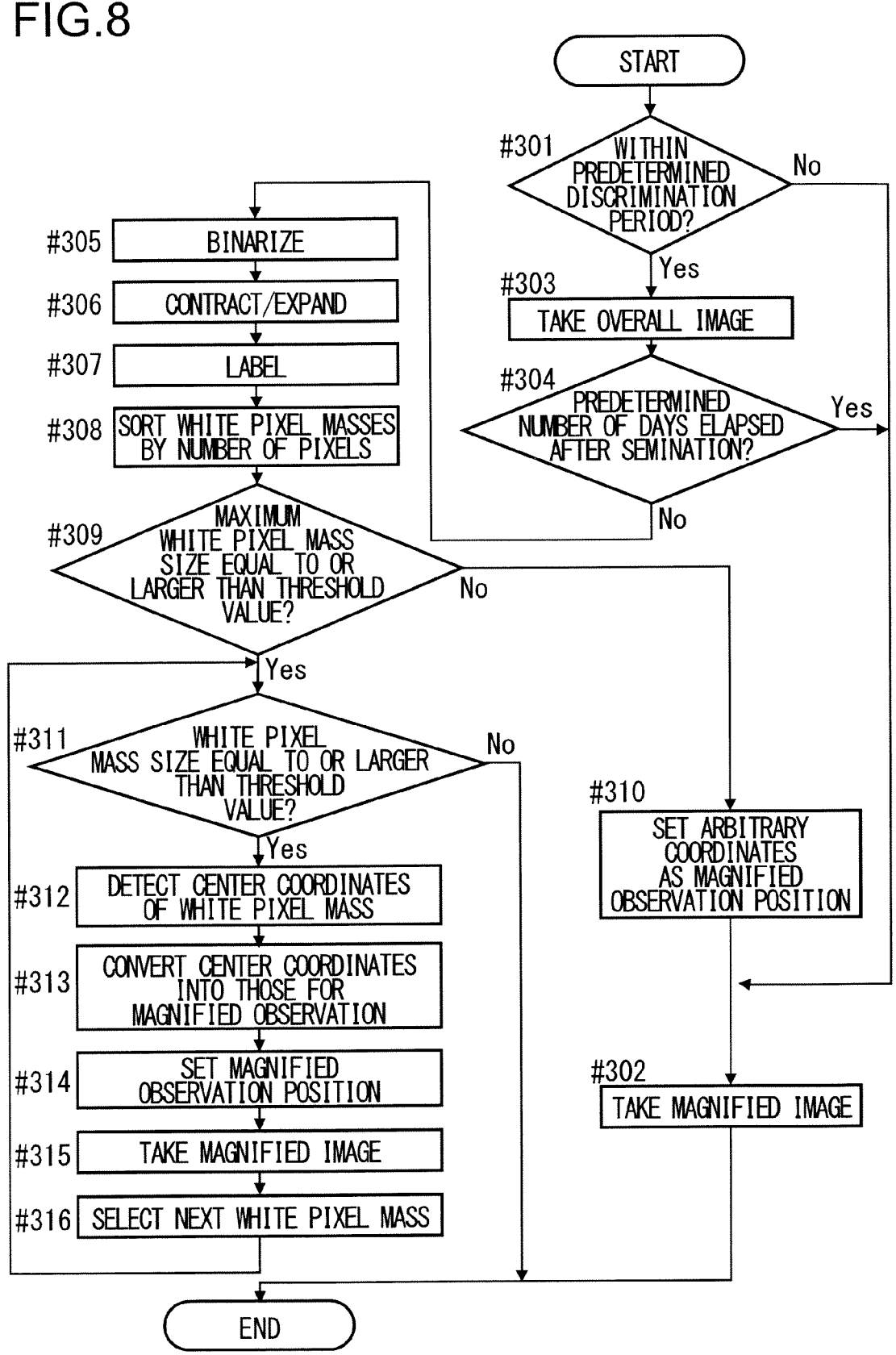
FIG. 8 is a flow chart showing the operation of observation processing in an observation processing according to a second embodiment of the invention.

Next, with respect to an observation program according to a second embodiment of the invention, operations related to its observation processing will be described along the flow shown in FIG. 8. FIG. 8 is a flow chart showing the operations related to observation processing in the observation program. The configuration in this embodiment is basically the same as that in the first embodiment described previously with reference to FIGS. 1 to 7, and therefore such components as are common to those of the first embodiment will be omitted from illustration and description.

When the observation program 220 according to the second embodiment is executed ("START" in FIG. 8), it first checks whether or not now is within the predetermined discrimination period (Step #301). If now is within the predetermined discrimination period ("Yes" at Step #301), the observation program 220 instructs the overall observation portion 10 in the observation device 1 to sense the entire container C to take an image of cells (Step #303).

Next, the observation program 220 checks whether or not the predetermined number of discrimination days have elapsed after semination of cells (Step #304). In this connection, the observation program 220 has previously made the time keeping portion 202 count the days and hours after semination, for example from the start of observation of cells. The predetermined number of discrimination days is a previously set number of days with respect to the timing with which to end discrimination of magnified observation target cell masses, is set at, for example, five days, and is stored in the observation timing holding portion 211 in the storage portion 210.

If, at Step #304, the predetermined number of discrimination days, namely five days, have elapsed after semination, for example, from the start of observation of cells ("Yes" at Step #304), the observation program 220 makes the magnified observation portion 20 take a magnified image (Step #302), and ends the flow of the sequence of operations related to observation processing ("END" in FIG. 8). That is, when five days pass from the start of observation, discrimination of cell masses to be taken as magnified observation targets is stopped, and their position information is no longer updated.

If, at Step #304, the predetermined number of discrimination days, namely five days, have not elapsed after semination, for example, from the start of observation of cells ("No" at Step #304), the observation program 220 executes binarization processing to distinguish between, of the overall image taken, a part not corresponding to a cell mass and a part corresponding to a cell mass by use of a predetermined threshold value (Step #305). The operation flow at subsequent Steps #305 through #316 is the same as that at Steps #204 through #215 in the first embodiment, and therefore their description will be omitted.

In time lapse observation, the above-described discrimination of magnified observation target cell masses is repeated every predetermined discrimination period until a magnified observation target cell mass is discriminated, and, on condition that the predetermined number of discrimination days (five days) have elapsed, the discrimination of magnified observation target cell masses is stopped. The predetermined discrimination period is a previously set period counted by the time keeping portion 202 with respect to the timing with which to execute discrimination of magnified observation target cell masses, is set at, for example, one day, and is stored in the observation timing holding portion 211 in the storage portion 210. The predetermined discrimination period and the predetermined number of discrimination days can be set as desired.

In this way, discrimination of magnified observation target cell masses is repeated every predetermined discrimination period (one day) until a magnified observation target cell mass is recognized, that is, until the time of occurrence of a cell mass is grasped, and this make it possible to automatically grasp the time of occurrence of a cell mass. Then, when the predetermined number of discrimination days (five days) have elapsed, the discrimination of magnified observation target cell masses is stopped, and thus it is possible to execute magnified observation of only those cell masses that have been identified in overall observation, and thus to proceed with observation efficiently until completion of growth.

The determination of whether or not to continue discrimination of magnified observation target cell masses may be made, instead of by a method whereby, as at Step #304, it is automatically made based on the number of days, by providing a window or other user interface that allow free setting by the user so that the determination of whether or not to continue discrimination of magnified observation target cell masses is delegated to the user.

(Embodiment 3)

Figure 9:
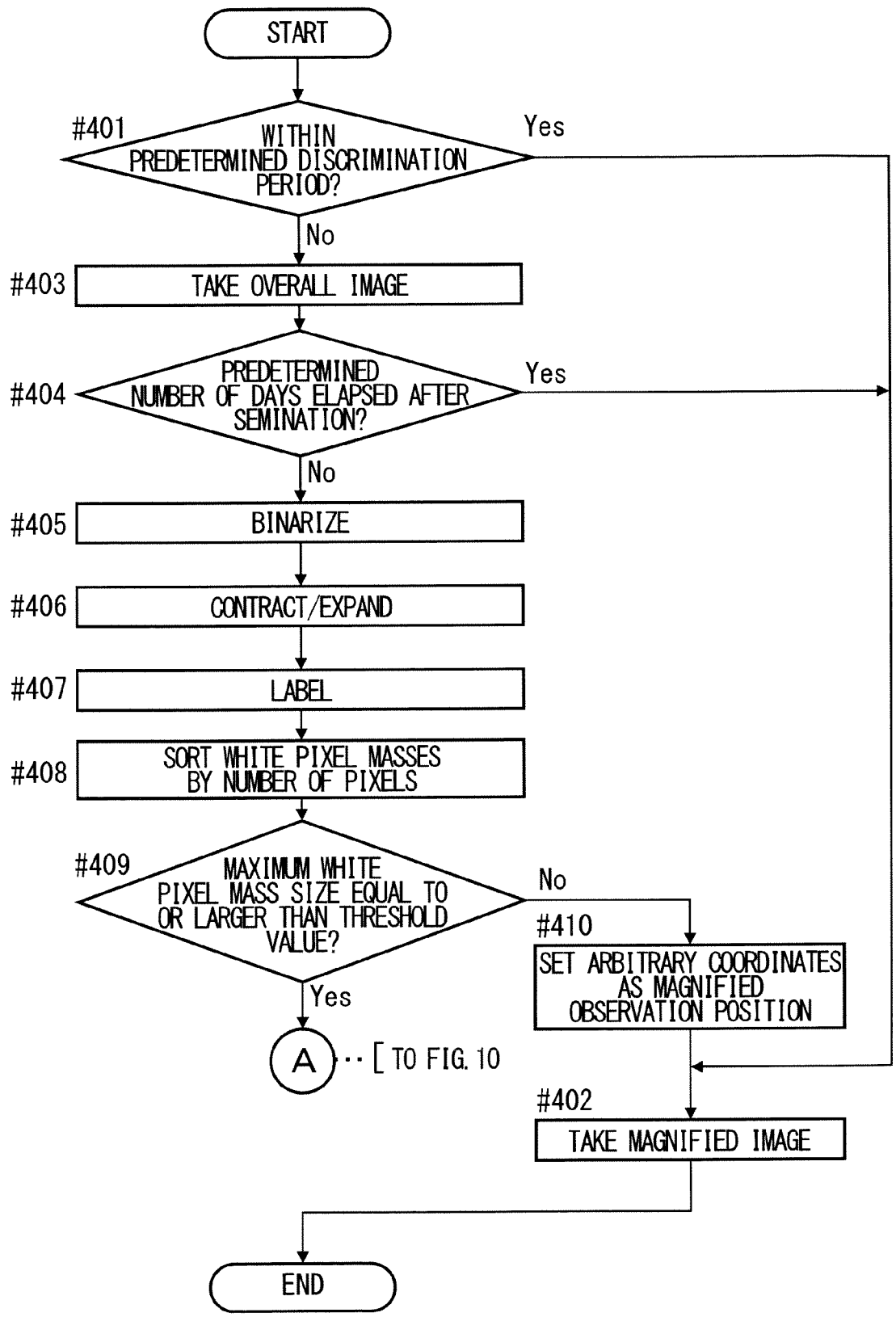
FIG. 9 is a flow chart showing the operation of observation processing in an observation processing according to a third embodiment of the invention.
Figure 10:
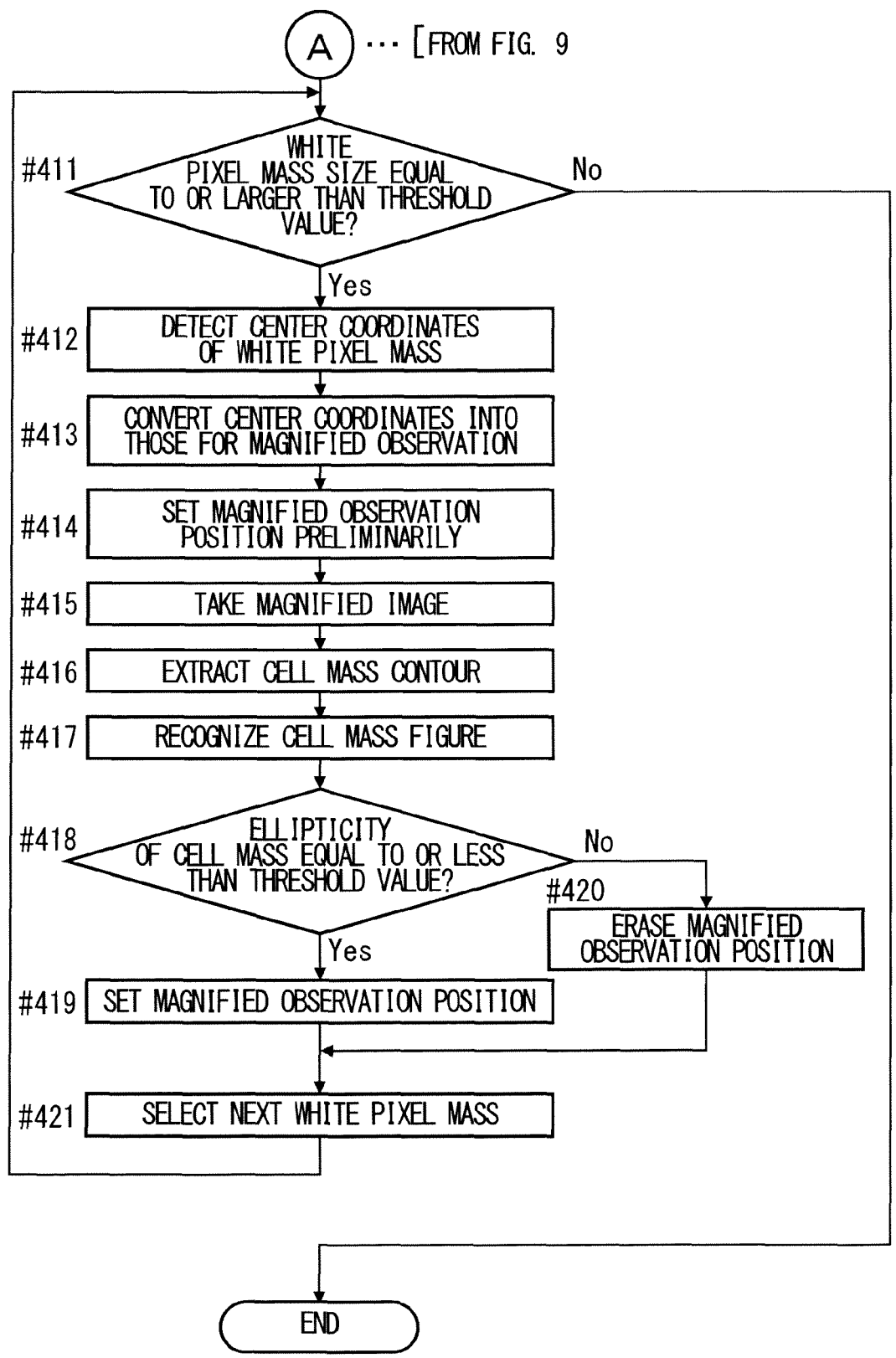
FIG. 10 is a continuation of the flow chart shown in FIG. 9 showing the operation of observation processing.

Next, with respect to an observation program according to a third embodiment of the invention, operations related to its observation processing will be described along the flow shown in FIGS. 9 and 10. FIG. 9 is a flow chart showing the operations related to observation processing in the observation program, and FIG. 10 is a continuation of the flow chart shown in FIG. 9 showing the operations related to observation processing. The configuration in this embodiment is basically the same as that in the first and second embodiments described previously, and therefore such components as are common to those of those embodiments will be omitted from illustration and description.

In the third embodiment, Steps #401 through #410 in the operation flow in FIG. 9 and Steps #411 through #413 in the operation flow in FIG. 10 are the same as in the operation flow in FIGS. 7 and 8, and therefore their description will be omitted.

The observation program 220 preliminarily sets the center coordinates of the cell mass that have been converted into those for magnified observation at Step #413 in FIG. 10 as a magnified observation position (Step #414). Then, the observation program 220 instructs the magnified observation portion 20 to take a magnified image of cells with respect to the magnified observation position within the container C (Step #415).

Subsequently, the observation program 220 extracts from the image taken in the magnified image sensing processing the contour of a cell mass (Step #416), and discriminates its figure (Step #417). Then, the observation program 220 checks whether or not the discriminated figure of the cell mass is a predetermined figure, that is, whether or not it has an ellipticity equal to or smaller than the threshold value (Step #418). The threshold value of ellipticity here which indicates the predetermined figure is set at, for example, 1.1, and is stored in the threshold value holding portion 214 in the storage portion 210. The threshold value of ellipticity indicating a predetermined figure of a cell mass can be set as desired. Any condition for determination of a predetermined figure of a cell mass other than ellipticity, for example roundness, may instead be set.

If, at Step #418, the ellipticity of the cell mass is equal to or smaller than the threshold value ("Yes" at Step #418), the observation program 220 definitively sets the center coordinates of the cell mass as the magnified observation position (Step #419). On the other hand, if the ellipticity of the cell mass is greater than the threshold value ("No" at Step #418), the observation program 220 erases the preliminarily set magnified observation position (Step #420). Then, the observation program 220 selects the next white pixel mass (cell mass) as the target of determination of whether or not it is a magnified observation target cell mass (Step #421), and returns to Step #411 to check whether or not the selected cell mass has a size equal to or larger than a predetermined size.

In this way, a cell mass having a predetermined figure is discriminated, and this makes it possible to automatically pick out cell masses having figures adequate for continued observation. As a result, it is possible to stop observation of cell masses that have grown to have distorted figures, and thus to proceed with observation of cell masses having adequate figures efficiently.

The determination of the figure of the cell mass at Step #418 may be made, instead of a method whereby it is explicitly made on the basis of a threshold value (for example, an ellipticity of 1.1), by a method whereby cell mass images are sorted according to whether their determination results are good or bad and are displayed on the monitor 204a (when ellipticity is the criterion, displayed in increasing order of ellipticity) and determination of up to what position they are suitable is delegated to the user.

(Embodiment 4)

Figure 11:
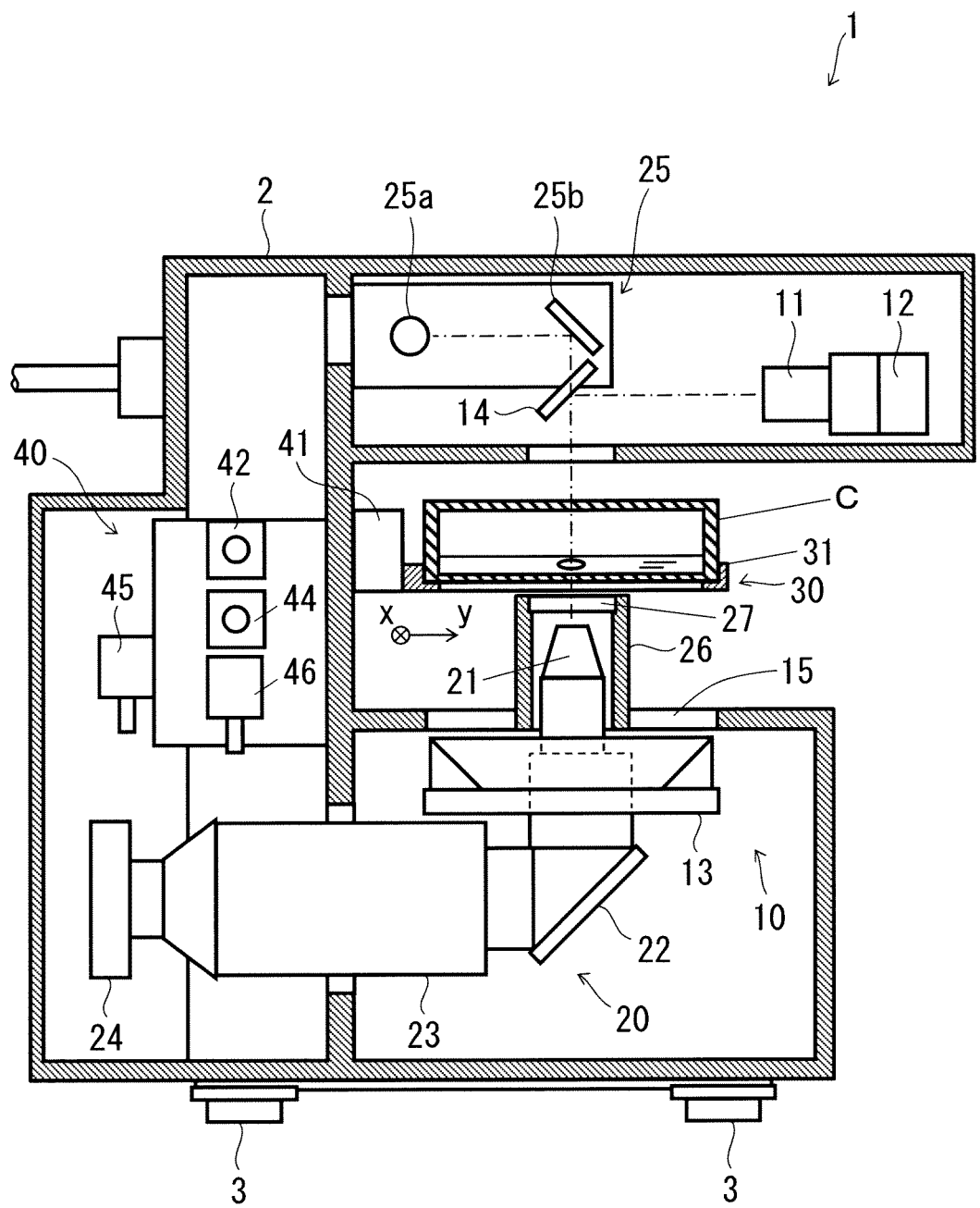
FIG. 11 is a vertical sectional side view of an observation device according to a fourth embodiment of the invention.

Next, the configuration of an observation device according to a fourth embodiment of the invention will be described with reference to FIG. 11. FIG. 11 is a vertical sectional side view of the observation device. The configuration in this embodiment is basically the same as that in the first embodiment described previously with reference to FIGS. 1 to 7, and therefore such components as are common to those of the first embodiment will be identified by the same reference signs as previously assigned, and will be omitted from illustration and description.

As shown in FIG. 11, in the observation device 1 according to the fourth embodiment, the overall observation portion 10 is provided with an overall observation optical system including a lens 11 and a reflective mirror 14, a CMOS camera 12 as an image sensing portion, a ring illuminator 13 as an overall observation illuminator, and an annular window 15.

The reflective mirror 14 is arranged above the movement space of the transport portion 30 which holds the container C, and is provided with such an inclination that the light shone to the container C is reflected approximately horizontally frontward. The reflective mirror 14 directs the light shone to the container C to the lens 11 frontward. The CMOS camera 12 is provided further frontward of the lens 11, and is arranged so that the image sensor surface of the CMOS camera 12 points toward the lens 11.

The ring illuminator 13 is arranged below the movement space of the transport portion 30, and is arranged so that the objective lens 21 part of the magnified observation portion 20 penetrates inside the ring illuminator 13. The ring illuminator 13 shines light obliquely upward, toward the center of the ring, and illuminates the observation target, that is, cells inside the container C on the transport portion 30 located above the ring illuminator 13. Accordingly, in the body 2, above the ring illuminator 13, an annular window 15 is provided. The annular window 15 is arranged so as to surround the objective lens cover 26. Thus, the light from the ring illuminator 13 passes through the annular window 15 and reaches the container C.

The overall observation portion 10 is configured and arranged such that the optical axis from the center of the ring illuminator 13 through the container C to the reflective mirror 14 coincides with, in the magnified observation portion 20, the optical axis from the reflective mirror 25b of the phase contrast illuminating portion 25 through the container C to the objective lens 21, and that their axial lines coincide with each other. The reflective mirror 14 is a half-mirror, which on one hand reflects the light from the ring illuminator 13 to direct it to the lens 11 and to the CMOS camera 12 and on the other hand transmits the light from the phase contrast illuminating portion 25 to direct it to the objective lens 21.

This makes it easy to make coordinates in the observation view field coincide between the overall observation portion 10 and the magnified observation portion 20. Moreover, after overall observation, simply by moving the container C in a comparatively narrow range, it is possible to reach the magnified observation position. This makes it possible to reduce the time required for observation and in addition perform observation with high precision.

(Embodiment 5)

Figure 12:
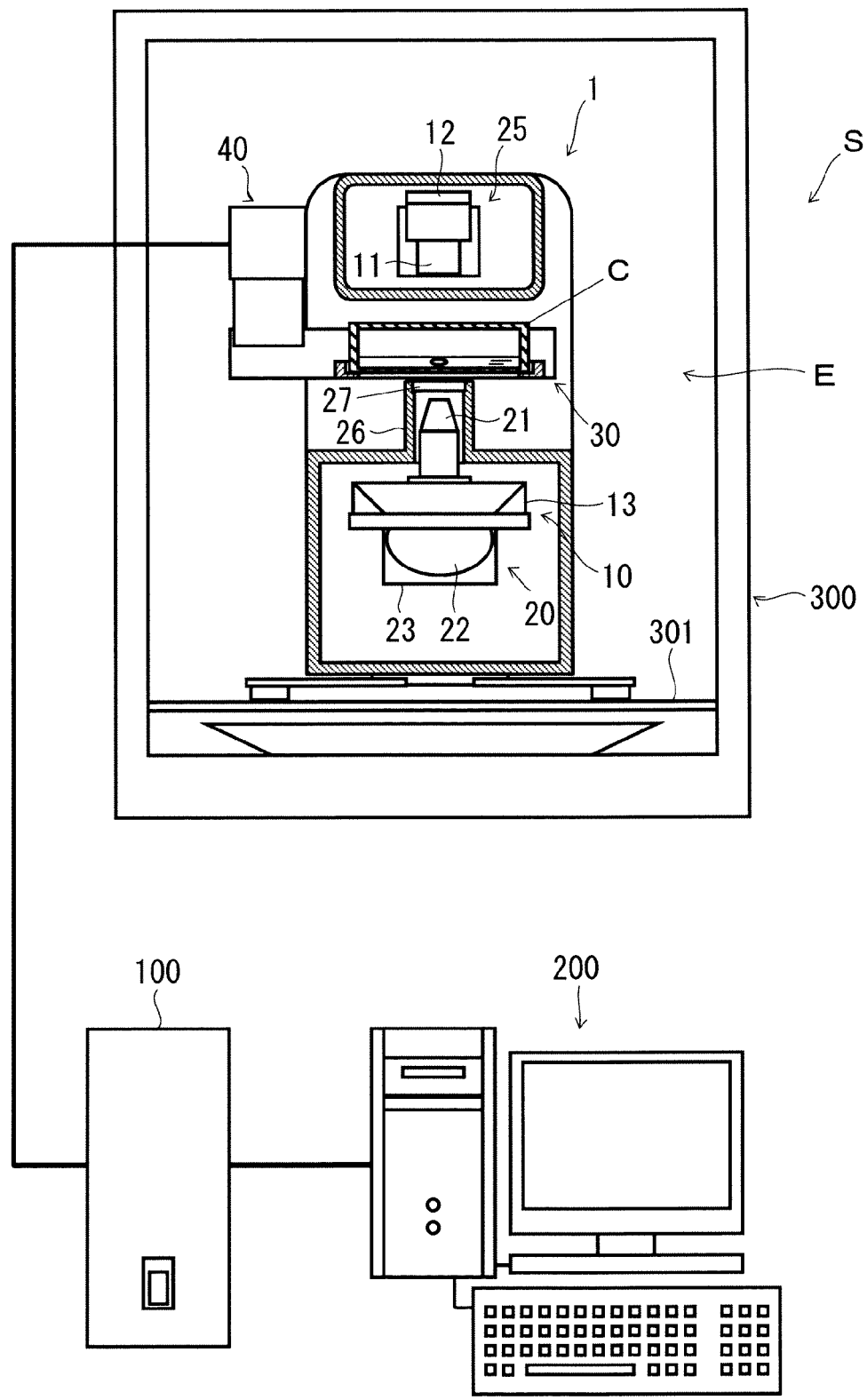
FIG. 12 is a configuration diagram of an observation device system according to a fifth embodiment of the invention.

Next, an observation device system according to a fifth embodiment of the invention will be described with reference to FIG. 12. FIG. 12 is a configuration diagram of the observation device system. The configuration in this embodiment is basically the same as that in the first embodiment described previously with reference to FIGS. 1 to 7, and therefore such components as are common to those of the first embodiment will identified by the same reference signs assigned previously, and will be omitted from illustration and description.

As shown in FIG. 12, in the observation system S according to the fifth embodiment, the observation device 1 is housed inside an incubator 300. The incubator 300 is an example of a storage chamber for culturing or storing cells, and forms a storage space E that is biologically and/or physically airtight. The observation device 1 is used in a state placed on a shelf 301 provided inside the incubator 300.

Here, the interior of the incubator 300 is typically maintained to provide a closed environment, for example, with a temperature of 37° C. and a humidity of 100%. Such an environment is likely to induce faults ascribable to humidity, such as degraded image quality resulting from fogging in the optical system and short-circuiting in electrical parts in the driving mechanism, camera, and illuminator. Accordingly, for arrangement inside an incubator 300 in particular, the observation device 1 needs to have a casing (body 2) that is airtight.

Inside the airtight casing of the observation device 1, the heat generated by the drive mechanism, camera, and illuminator accumulates, stagnates around the objective lens 21, and tends to dissipate upward. By contrast, giving the window 27 of the objective lens cover 26 an area in a range of about 1 mm to 10 mm, that is, an area that is minimal without attenuating the amount of illumination light, and giving the objective lens cover 26 a minimal area in its part close to the bottom face of the container C, helps suppress the effect of heat resulting from almost no gap being left between the bottom face of the container C and the objective lens cover 26 and hence no air passing there. At the same time, making the objective lens cover 26 cover only around the objective lens 21 helps increase the surface area of the objective lens cover 26, and this permits heat to dissipate sideways with respect to the objective lens cover 26, where air passes easily, and thereby to suppress conduction of heat to the container C.

Along with these benefits, also with a configuration where the observation device 1 is provided inside the incubator 300, it is possible to provide an observation device 1 that, in observation of cells being cultured inside a container C, allows observation of the entire container C for identification of cells having occurred and in addition allows magnification of the identified cell masses for observation of their details. It is also possible to provide an observation system S that allows continuous observation of the identified cell masses from their occurrence till the completion of their growth.

(Embodiment 6)

Figure 13:
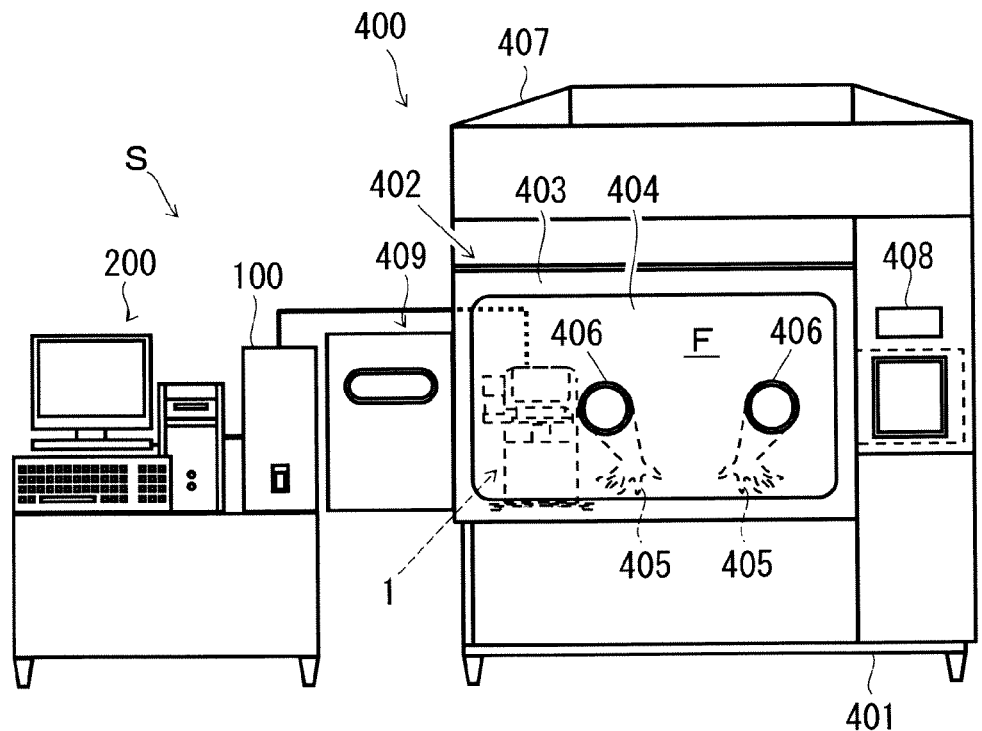
FIG. 13 is a configuration diagram of an observation device system according to a sixth embodiment of the invention.
Figure 14:
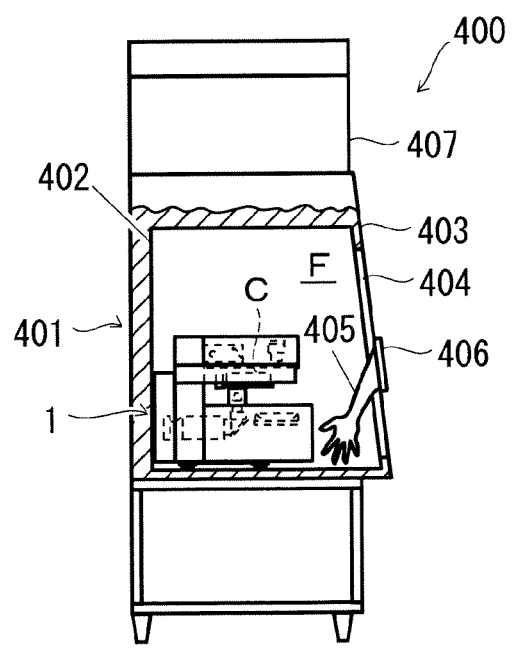
FIG. 14 is a partial sectional side view of the isolator shown in FIG. 13.

Next, an observation device system according to a sixth embodiment of the invention will be described with reference to FIGS. 13 and 14. FIG. 13 is a configuration diagram of the observation device system, and FIG. 14 is a partial sectional side view of the isolator shown in FIG. 13. The configuration in this embodiment is basically the same as that in the first embodiment described previously with reference to FIGS. 1 to 7, and therefore such components as are common to those of the first embodiment will be identified by the same reference signs as previously assigned, and will be omitted from illustration and description.

In the observation system S according to the sixth embodiment, the observation device 1 is housed inside an isolator 400.

The isolator 400 has a case 402 provided in a central part of its cabinet 401. The case 402 forms a biologically and/or physically airtight operation space F in which to perform operations related to culturing, processing, and observation of cells. On the front side of the case 402, a front door 403 is provided so as to be freely opened and closed. The front door 403 is provided with a window 404 formed of glass to permit a view inside the operation space F from outside.

The window 404 in the front door 403 is provided with gloves 405 through which to perform operations inside the operation space F. The gloves 405 are so provided as to extend from the window 404 in the case 402 into the operation space F. The window 404 has, in its parts where the gloves 405 are fitted to it, openings 406. The operator wears the gloves 405 by putting his hands into them through the openings 406, and, while viewing the operation space F inside the airtight case 402 across the window 404, performs operations. Two of the gloves 405 are arranged side by side in the horizontal direction. The number of gloves 405, and hence of openings 406, is not limited to two, but may instead be three, four, or more.

The isolator 400 is further provided with a gas adjustment portion 407 in a top part of the case 402, a main unit operation portion 408 on the right of the case 402 as seen from in front, and an incubator 409 on the left.

Also with this configuration where the observation device 1 is provided inside an isolator 400, it is possible to provide an observation device 1 that, in observation of cells being cultured inside a container C, allows observation of the entire container C for identification of cells having occurred and in addition allows magnification of the identified cell masses for observation of their details. It is also possible to provide an observation system S that allows continuous observation of the identified cell masses from their occurrence till the completion of their growth. The observation device 1 may instead be placed inside an incubator 409.

Embodiment 7

Figure 15:
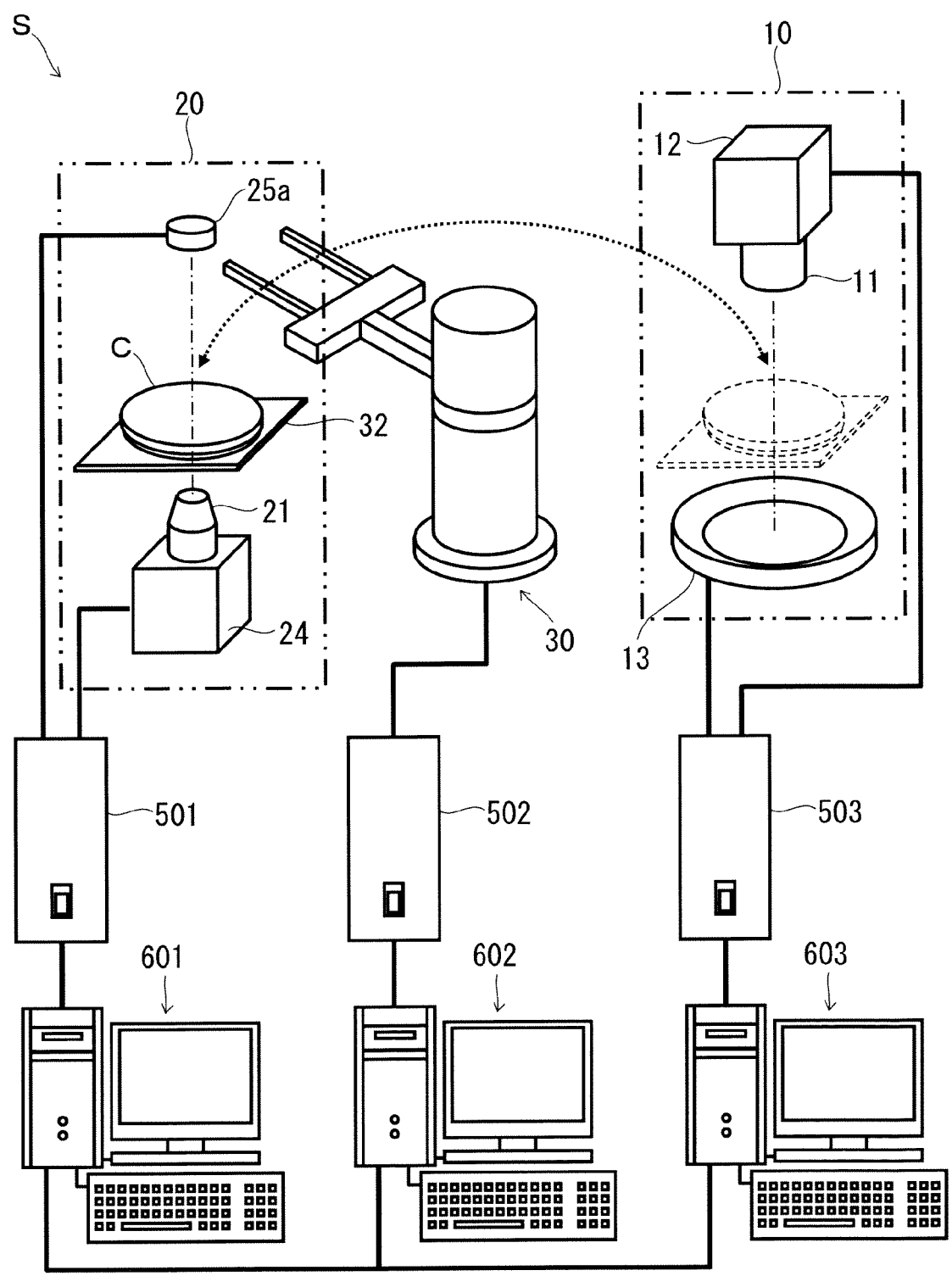
FIG. 15 is a configuration diagram of an observation device system according to a seventh embodiment of the invention.

Next, an observation device system according to a seventh embodiment of the invention will be described with reference to FIG. 15. FIG. 15 is a configuration diagram of the observation device system. The configuration in this embodiment is basically the same as that in the first embodiment described previously with reference to FIGS. 1 to 7, and therefore such components as are common to those of the first embodiment will be identified by the same reference signs as previously assigned, and will be omitted from illustration and description.

As shown in FIG. 15, the observation system S according to the seventh embodiment is provided with an overall observation portion 10, a magnified observation portion 20, and a transport portion 30, and these are provided independently of one another. The overall observation portion 10, the magnified observation portion 20, and the transport portion 30 are provided with control devices 501 to 503 which control them individually and computers 601 to 603 which send commands to those individually. The three computers 601 to 603 are connected together across network cables so that they can communicate with one another, and this permits overall observation, magnified observation, and the transport of the container C to be executed in a coordinated fashion.

The coordination among the three computers may be governed by an additional, separate computer. Instead, a single computer may be used which sends instructions to the control devices 501 to 503. Instead, a single computer and a single control device may be used so that the overall observation portion, the magnified observation portion, and the transport portion are controlled from the single computer and control device.

Although, in FIG. 15, the transport portion 30 is configured to transport the container C by rotating it between the overall observation portion 10 and the magnified observation portion 20, it may instead be configured, as in the first embodiment, to transport the container C by translating it. The container C is placed on a tray 32 common to the overall observation portion 10 and the magnified observation portion 20. The tray 32 is positioned with respect to the overall observation portion 10 and the magnified observation portion 20, and the container C is positioned with respect to the tray 32.

Also with this configuration where the overall observation portion 10, the magnified observation portion 20, and the transport portion 30 are independent of one another and are controlled individually, it is possible to provide an observation device 1 that, in observation of cells being cultured inside a container C, allows observation of the entire container C for identification of cells having occurred and in addition allows magnification of the identified cell masses for observation of their details. It is also possible to provide an observation system S that allows continuous observation of the identified cell masses from their occurrence till the completion of their growth.

In a narrow operation space as inside an incubator or an isolator, configuring an overall observation portion, a magnified observation portion, and a transport portion as mechanically separate units allows their flexible design and arrangement and thus allows efficient use of the operation space.

It should be understood that the embodiments by way of which the present invention has been described are in no way meant to limit the scope of the invention, and that the invention may be implemented with many modifications and variations made without departing from the spirit of the invention.

For example, although the embodiments described above assume observation using a single culture container, it is also possible to perform observation on a plurality of culture containers simultaneously by using a tray on which a plurality of culture containers can be placed.

Although the embodiments described above assume the use of a CMOS camera 12 in the image sensing portion of the overall observation portion 10 and a CCD camera 24 in the image sensing portion of the magnified observation portion 20, either of those cameras may be a CMOS or a CCD camera.

INDUSTRIAL APPLICABILITY

The present invention finds applications in observation devices, observation programs, observation methods, and observation systems for the observation of a sample such as cells.

LIST OF REFERENCE SIGNS

S observation system
1 observation device
2 body (casing)
10 overall observation portion
11 lens (overall observation optical system)
12 CMOS camera (image sensing portion)
13 ring illuminator (overall observation illuminator)
20 magnified observation portion
21 objective lens (magnified observation optical system, lens portion)
22 reflective mirror (magnified observation optical system)
23 zoom lens (magnified observation optical system)
24 CCD camera (image sensing portion)
25 phase contrast illuminating portion (magnified observation illuminator)
26 objective lens cover (cover member)
27 window
30 transport portion
100 control device
200 computer
201 data processing portion
202 time keeping portion
210 storage portion
211 observation timing holding portion (setting portion)
214 threshold value holding portion (setting portion)
220 observation program
C container
D gap

The invention claimed is:

1. A non-transitory tangible machine-readable medium storing an observation program for causing a computer to execute processing, the processing comprising:
overall image sensing processing for taking an image of a sample through taking an image of an entire container containing the sample and a solution;
sample mass discrimination processing for discriminating from the image taken in the overall image sensing processing a sample mass, which is a mass of a plurality of pieces of the sample;
coordinate detection processing for detecting coordinates of a center of the sample mass discriminated in the sample mass discrimination processing;
magnified image sensing processing for taking an image of the sample mass on a magnified scale about, as a center, the coordinates detected in the coordinate detection processing; and
time keeping processing for counting days and hours from a start of observation of the sample, wherein
in the sample mass discrimination processing, discrimination of the magnified observation target sample mass is repeated every predetermined period counted in the time keeping processing with respect to sample mass discrimination until, from the image taken in the overall image sensing processing. any of sample masses, which are each a mass of a plurality of pieces of the sample, is recognized as a magnified observation target sample mass having a size equal to or larger than a predetermined size, and the discrimination of the magnified observation target sample mass is stopped on condition that a predetermined number of days have elapsed, and
in the coordinate detection processing, on condition that a magnified observation target sample mass having a size equal to or larger than the predetermined size has been recognized in the sample mass discrimination processing, coordinates of a center of the magnified observation target sample mass are detected.

2. The non-transitory tangible machine-readable medium according to claim 1, wherein, in the coordinate detection processing, arbitrary coordinates are detected on condition that no magnified observation target sample mass has been recognized in the sample mass discrimination processing.

3. An observation system comprising:
an overall observation portion including
an illuminator which shines light on a sample inside a container containing the sample and a solution and
an optical system which guides light for observation of the sample,
the overall observation portion taking an image of the sample through taking an image of the entire container;
a time keeping portion which counts days and hours from a start of observation of the sample;
a data processing portion which repeats discrimination of a sample mass, which is a mass of a plurality of pieces of the sample, every predetermined period counted by the time keeping portion with respect to sample mass discrimination until a sample mass having a size equal to or larger than a predetermined size is recognized from the image taken by the overall observation portion, the data processing portion detecting coordinates of a center of the recognized sample mass having a size equal to or larger than the predetermined size;
a magnified observation portion including
an illuminator which shines light on the sample inside the container and
an optical system which guides light for observation of the sample,
the magnified observation portion taking an image of the sample mass on a magnified scale about, as a center, the coordinates detected by the data processing portion; and
a setting portion which sets
a sample mass discrimination repetition deadline until which the data processing portion recognizes the sample mass having a size equal to or larger than the predetermined size,
timing with which the magnified observation portion takes the image, and
an observation deadline until which the sample is observed.

4. The observation system according to claim 3, wherein the data processing portion detects arbitrary coordinates on condition that no magnified observation target sample mass has been recognized.

5. A non-transitory tangible machine-readable medium storing an observation program for causing a computer to execute processing, the processing comprising:

overall image sensing processing for taking an image of a sample through taking of a container containing the sample and a solution:

sample mass discrimination processing for discriminating from the image taken in the overall image sensing processing a sample mass. which is a mass of a plurality of pieces of the sample;

coordinate detection processing for detecting coordinates of a center of the sample mass discriminated in the sample mass discrimination processing; and magnified image sensing processing for taking an image of the sample mass on a magnified scale about, as a center, the coordinates detected in the coordinate detection processing, wherein in the sample mass discrimination processing, when the discriminated sample mass has a figure with a predetermined roundness, or when a ratio of a major axis length to a minor axis length of an ellipse surrounding a contour of the discriminated sample mass is equal to or less than a predetermined threshold value, the discriminated sample mass is found to have a predetermined figure, in the coordinate detection processing, on condition that the sample mass has been found to have the predetermined figure in the sample mass discrimination processing, the coordinates of the center of the sample mass are detected, and in the coordinate detection processing, arbitrary coordinates are detected on condition that the sample mass has been found not to have the predetermined figure in the sample mass discrimination processing.

6. A non-transitory tangible machine-readable medium storing an observation program for causing a computer to execute processing, the processing comprising:

overall image sensing processing for taking an image of a sample through taking of a container containing the sample and a solution;

sample mass discrimination processing for discriminating from the image taken in the overall image sensing processing a sample mass, which is a mass of a plurality of pieces of the sample;

coordinate detection processing for detecting coordinates of a center of the sample mass discriminated in the sample mass discrimination processing;

magnified image sensing processing for taking an image of the sample mass on a magnified scale about, as a center, the coordinates detected in the coordinate detection processing; and time keeping processing for counting days and hours from a start of observation of the sample, wherein in the sample mass discrimination processing, when the discriminated sample mass has a figure with a predetermined roundness, or when a ratio of major axis length to a minor axis length of an ellipse surrounding a contour of the discriminated sample mass is equal to or less than a predetermined threshold value, the discriminated sample mass is found to have a predetermined figure, in the coordinate detection processing, on condition that the sample mass has been found to have the predetermined figure in the sample mass discrimination processing, the coordinates of the center of the sample mass are detected, and in the sample mass discrimination processing, the discrimination is repeated every predetermined period counted in the time keeping processing with respect to sample mass discrimination until the sample mass having the predetermined figure is recognized, and the discrimination is stopped on condition that a predetermined number of days have elapsed.

7. An observation system comprising:

an overall observation portion including
  an illuminator which shines light on a sample inside a container containing the sample and a solution and
  an optical system which guides light for observation of the sample,
the overall observation portion taking an image of the sample through taking an image of the entire container;

a time keeping portion which counts days and hours from a start of observation of the sample;

a data processing portion which repeats discrimination of a sample mass, which is a mass of a plurality of pieces of the sample, every predetermined period counted by the time keeping portion with respect to sample mass discrimination until a sample mass having a predetermined figure is recognized from the image taken by the overall observation portion, the data processing portion detecting coordinates of a center of the recognized sample mass having the predetermined figure;

a magnified observation portion including
  an illuminator which shines light on the sample inside the container and
  an optical system which guides light for observation of the sample,
the magnified observation portion taking an image of the sample mass on a magnified scale about, as a center, the coordinates detected by the data processing portion; and a setting portion which sets
  a sample mass discrimination repetition deadline until which the data processing portion recognizes the sample mass having the predetermined figure,
  timing with which the magnified observation portion takes the image, and an observation deadline until which the sample is observed.

* * * * *